United States Patent
Sundram et al.

(10) Patent No.: US 7,229,653 B2
(45) Date of Patent: *Jun. 12, 2007

(54) INCREASING THE HDL LEVEL AND THE HDL/LDL RATIO IN HUMAN SERIUM BY BALANCING SATURATED AND POLYUNSATURATED DIETARY FATTY ACIDS

(75) Inventors: Kalyana Sundram, Petaling Java (MY); Daniel Perlman, Arlington, MA (US); Kenneth C. Hayes, Wellesley, MA (US)

(73) Assignee: Brandeis University, Waltham, MA (US)

( * ) Notice: Subject to any disclaimer, the term of this patent is extended or adjusted under 35 U.S.C. 154(b) by 181 days.

This patent is subject to a terminal disclaimer.

(21) Appl. No.: 10/434,907

(22) Filed: May 9, 2003

(65) Prior Publication Data
US 2003/0198728 A1 Oct. 23, 2003

Related U.S. Application Data

(63) Continuation of application No. 09/828,448, filed on Apr. 6, 2001, now Pat. No. 6,630,192, which is a continuation-in-part of application No. 09/241,603, filed on Feb. 1, 1999, now abandoned, which is a continuation-in-part of application No. 08/755,591, filed on Nov. 25, 1996, now Pat. No. 5,874,117, which is a continuation-in-part of application No. 08/626,461, filed on Apr. 2, 1996, now Pat. No. 5,843,497, which is a continuation-in-part of application No. 08/418,641, filed on Apr. 7, 1995, now Pat. No. 5,578,334.

(51) Int. Cl.
A23D 9/00 (2006.01)

(52) U.S. Cl. .......................................... 426/2; 424/439

(58) Field of Classification Search ................... 426/2, 426/601, 603, 607
See application file for complete search history.

(56) References Cited

U.S. PATENT DOCUMENTS

| | | | |
|---|---|---|---|
| 1,432,635 A * | 10/1922 | Stevens ....................... 426/585 |
| 2,659,676 A | 11/1953 | Howards et al. |
| 2,996,388 A | 8/1961 | Lindsay |
| 3,011,893 A | 12/1961 | Kneeland |
| 3,268,340 A | 8/1966 | Babayan et al. |
| 3,353,964 A | 11/1967 | Selden |
| 3,488,198 A | 1/1970 | Bundus |
| 3,634,100 A | 1/1972 | Merksem et al. |
| 3,649,295 A * | 3/1972 | Bernhart ...................... 426/607 |
| 3,843,828 A | 10/1974 | Arndt |
| 4,568,556 A | 2/1986 | McCoy |
| 4,614,663 A | 9/1986 | Rule |
| 4,721,626 A | 1/1988 | Rule |
| 4,803,087 A | 2/1989 | Karinen |
| 4,804,555 A | 2/1989 | Marschner et al. |
| 4,842,884 A | 6/1989 | Bookwalter et al. |
| 5,000,975 A | 3/1991 | Tomarelli |
| 5,063,074 A | 11/1991 | Kahn et al. |
| 5,223,285 A * | 6/1993 | DeMichele .................. 426/801 |
| 5,380,544 A * | 1/1995 | Klemann ..................... 426/607 |
| 5,382,442 A * | 1/1995 | Perlman ...................... 426/607 |
| 5,393,551 A | 2/1995 | Arcadipane |
| 5,462,755 A | 10/1995 | Mehnert |
| 5,514,407 A * | 5/1996 | Perlman ...................... 426/601 |
| 5,578,334 A * | 11/1996 | Sundram et al. ................ 426/2 |
| 5,580,600 A | 12/1996 | Strong et al. |
| 5,643,621 A | 7/1997 | Mehnert |
| 5,843,497 A * | 12/1998 | Sundram et al. ............ 424/439 |
| 5,874,117 A * | 2/1999 | Sundram et al. ................ 426/2 |
| 6,630,192 B2 | 10/2003 | Sundram et al. |

FOREIGN PATENT DOCUMENTS

| | | |
|---|---|---|
| DE | 24 44 213 A1 | 3/1975 |
| EP | 0151450 A2 | 8/1985 |
| EP | 01262753 | 12/2002 |
| GB | A-1245539 | 9/1971 |
| GB | 2 093 679 A | 9/1982 |
| GB | 2 261 304 A | 3/1995 |
| GB | 2 281 304 A | 3/1995 |
| JP | 55064756 | 5/1980 |
| WO | WO 95/06414 | 3/1995 |

OTHER PUBLICATIONS

Swern 1979 Baileys Industrial Oil and Fat Products vol. 1, 4th edition John Wiley & Sons New York p. 311-332 and 363-368.*

(Continued)

Primary Examiner—Carolyn Paden
(74) Attorney, Agent, or Firm—Foley & Lardner LLP

(57) ABSTRACT

A method of increasing the HDL concentration and the HDL/LDL concentration ratio in human serum by providing a balance between a sufficient and required proportion of cholesterol-free saturated fatty acids in the daily dietary fat of the human and a sufficient and required, but not excessive, proportion of polyunsaturated fatty acids comprising linoleic acid in dietary fat, while the remaining proportion of fatty acids and energy from the dietary fat is provided by monounsaturated fatty acids comprising oleic acid. Also described are compositions, including fat compositions and filled dairy products, containing such balanced fatty acid proportions.

42 Claims, 1 Drawing Sheet

OTHER PUBLICATIONS

Figure 1:
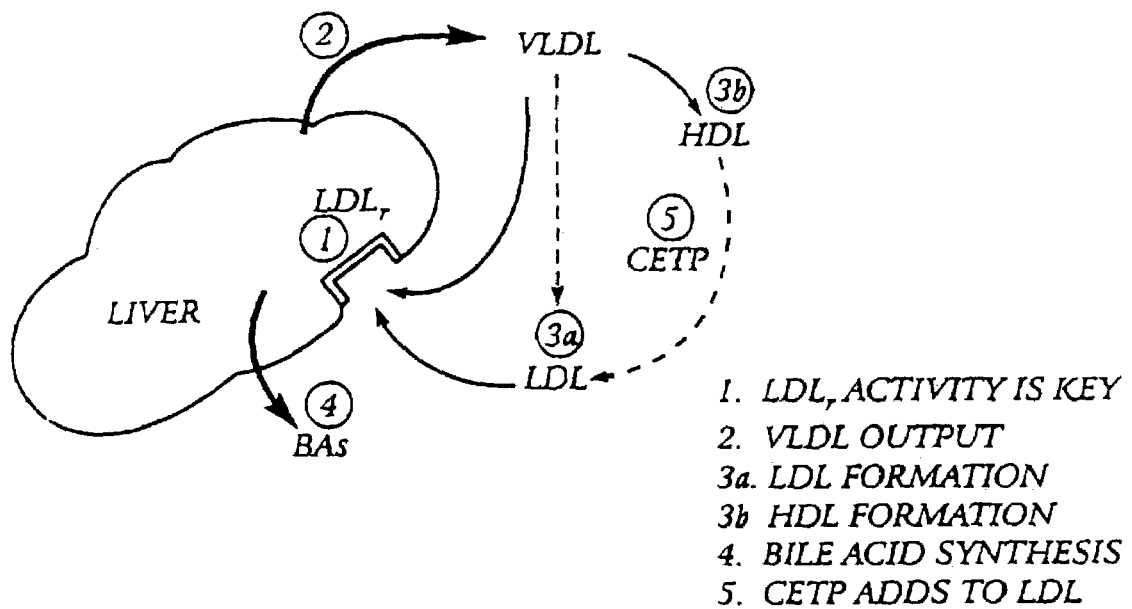

Wong et al., Fundamentals of Dairy Chemistry, Third Edition, 1988, Van Nostrand Reinhold Company, New York, pp. 743-744.*
"The Use of Palm Oil Products in Margarines". PORIM Technology publication. Aug. 1981, No. 5. Palm Oil Research Institute of Malaysia.*
Wood, R. et al. 1993. J. Nutri. Biochem 4:286-297.*
Hornstra, G. 1988. Oleagineux 43(2)75-81.*
Cottrell, R. 1991. Am. J. Clin. Nutr. 53:989S.*
"Physical and Chemical Characteristics of Oils, Fats, and Waxes", David Firestone, 1999.
"Composition of Foods—Fats and Oils, Raw, Processed, Prepared", James B. Reeves, III, et al., Consumer and Food Economics Institute, Agriculture Handbook No. 8-4, Jun. 1979, pp. 45 and 57. Agriculture Handbook No. 8-4, U.S.D.A. Science and Education Administration, *Composition of Foods: Fats and Oils*.
Berry et al., "Physicochemical characteristics of palm olein and soybean oil blends," *Palm Oil Technol. Eighties, Rep. Proc. Int. Conf*, pp. 483-498 (1981) (pub. 1983).
Charnock et al., "Dietary modulation of lipid metabolism and mechanical performance of the heart," *3rd Int. Symp. on Lipid Metabolism in the Normal and Ischemic Heart* (Sep. 9-10, 1991).
Choi et al., "Effect of dietary n-3 polyunsaturated fatty acids on cholesterol synthesis and degradation in rats of different ages," *Lipids* 24(1):45-50 (1989).
Demacker et al., "Increased Removal of remnants of triglyceride-rich lipoproteins on a diet rich in polyunsaturated fatty acids," *European J. of Clin. Invest.* 21:197-203 (1991).
Grundy and Denke, "Dietary Influences on serum lipids and lipoproteins," *J. Lipid Research* 31:1149-1172 (1990).
Grundy, "Comparison of Monounsaturated Fatty Acids and Carbohydrates for Lowering Plasma Cholesterol," *N. Eng. J. Med.* 314:745-748 (1986).
Grundy et al., "Influence of stearic acid on cholesterol metabolism relative to other long-chain fatty acids[1-3]," *American J. Clin. Nutr.* 60(suppl.):9865-9905 (1994).
Fujikawa, "Manufacture of Salad Oil," *Jpn. Kokai Tokkyo Koho IP* 61,293,389 [86,293,389] (Dec. 24, 1986).
Haga, "Manufacture of edible Oils," *Jpn. Kokai Tokkyo Koho IP* 61,296,096 [86,296,096] (Dec. 26, 1986).
Han et al., "Effect of palm oil blending on the thermal and oxidative stability of soybean oil," *Han'guk Siko'um Kwahakhoechi* 23(4):465-70 (1991).
Hayes et al., "Dietary saturated fatty acids (12:0, 14:0, 16:0) differ in their impact on plasma cholesterol and lipoproteins in nonhuman primates[1-4]," *Am. J. Clin. Nutr.* 53:491-498 (1991).
Hayes and Kholsa, "Dietary fatty acid thresholds and cholesterolemia," *FASEB* 6:2600-2607 (1992).
Hegsted et al., "Quantitative Effects on Dietary Fat on Serum Cholesterol in Man," *Amer. J. of Clin. Nutr.* 17:281-295 (1965).
Hegsted et al., "Dietary fat and serum lipids: an evaluation of the experimental data[1-4]," *Amm. J. of Clin. Nutr.* 57:875-883 (1993).
Heyden, "Polyunsaturated and Monounsaturated Fatty Acids in the Diet Prevent Coronary Heart Disease via Cholesterol Reduction," *Ann. Nutr. Metab.* 38:117-122 (1994).
Jacobs et al., "Variability in Individual Serum Cholesterol Response to Change in Diet," *Arteriosclerosis*, 3:349-356 (1983).
Kajimoto et al., "Influence of blend ratio of vegetable oils on their thermal oxidation and decomposition of tocopherol," *Nippon Eiyo, Shokuryo Gakkaishi* 44(6):499-505 (1991).
Katan et al., "Effects of fats and fatty acids on blood lipids in humans: an overview1-4,"*Am. J. Clin. Nutr*, 60(suppl):1017S-1022S (1994).
Khosla and Hayes, "Dietary fat saturation in rhesuss monkeys affects LDL concentrations by modulating the independent production of LDL apolipoprotein B," *Biochem. Biophys. Acta* 1083:46-56 (1991).
Khosla and Hayes, "Comparison between the effects of dietary saturated (16:0), monounsaturated (18:1), and polyunsaturated (18:2) fatty acids on plasma lipoprotein metabolism in cebus and rhesus monkeys fed cholesterol-free diets," *Am. J. Clin. Nutr.* 55:51-62 (1992).

Kifli et al., "Physical properties of interesterified palm oil/palm oil fractions with other vegetable oils," *Palm Oil, Prod. Technol. Eighties, Rep. Proc. Int. Conf.* pp. 303-314 (1981) (published 1983).
Kim, "Relationship between the triacylglycerol composition and foaming of mixed coconut oil under deep-fat frying," *Agric. Biol. Chem.* 52(3):693-699 (1988).
Lim et al., "Oxidative stability of Malaysian palm oil and its blends,." *Yukagaku* 39(12):1045-1049 (1990).
Litherland et al., "Preparation of chocolate fats by wet fractionation of soya oil," Abst. of EP 428,200 May 22, 1991, GB 89/25,943 (Nov. 16, 1989).
Majumdar et al., "Vanaspatl and margarine fat base from palm oil and palm stearin by corandomization with cottonseed oil," *J. Oil Techol. Assoc. India* 18(2):37-38 (1986).
Mensink and Katan, "Effect of Dietary Fatty Acids on Serum Lipids and Lipoproteins," *Arteriosclerosis and Thrombosis* 12:911-919 (1992).
Murakami et al., "Effect of processed oils and fats on cholesterol metabolism. IV. Effect of palm stearin and changes in its effect by blending with soybean oil and further randomizing," *Yukagaku* 41(3):196-202 (1992).
Murakami et al., "Effect of processed oils and fats on cholesterol metabolism. V. Effect of lard, its blend with palm olein and their randomized oil," *Yukagaku* 41(7):530-537 (1992).
Pronczuk et al., "Dietary myristic, palmitic, and linoleic acids modulate cholesterolemia in gerbils," *FASEB J.* 8:1191-1200 (1994).
Siguel and Maclure, "Relative Activity of Unsaturated Fatty Acid Metabolic Pathways in Humans," *Metabolism* 36:664-669 (1987).
Sundram et al., "Dietary palmitic acid results in lower serum cholesterol than does a lauric-myristic acid combination in normolipemic humans," *Am. J. Clin. Nutr.* 59:841-846 (1994).
Sundram et al., Fat (Fatty Acid) Modulation of Metabolism (2549-2554) *FASEB J.* 9:A440 (1995) (Abstract).
Suzuki et al., "Fat and oil compositions for frying and spraying,". *Jpn. Kokai Tokkyo Koho* JP 01,262,754 [89,262,754] (Oct. 19, 1989).
Wai, "A critical review of the cholesterolaemic effects of palm oil," *Food and Nutrition Bulletin* 15:112-123 (1994).
Willet and Sacks, "Chewing the Fat—How Much and What Kind," *N. Eng. J. of Med.* 324:121-123 (1991).
Berry, Shiv K., "Physico-chemical Characteristics of Palm Olein and Soybean Oil Blends," *Palm Oil Product Technology in the Eighties* (1983) 483-498, The Incorporated Society of Planters, Kuala Lumpur.
Formo, et al., *Bailey's Industrial Oil and Fat Products—vol. 1, Fourth Edition*, 379, John Wiley & Sons, New York.
Han, Yoon-Sook, "Effect of Palm Oil Blending on the Thermal and Oxidative Stability of Soybean Oil", *Korean J. Food Sci. Technol.*, 23(4):465-470 (1991).
Reeves, James B. and Weihrauch, John L., "Composition of Foods Fats and Oils Raw Processed Prepared,"*Agriculture Handbook* No. 8-4 (1979) 1-142, Science and Education Administration U.S. Department of Agriculture, Washington, D.C.
*Spectrum Organic Products, Inc.*, v. *GFA Brands, Inc. and Brandeis University*, First Amended Complaint for Declaratory Judgment of Non-Infringement and Invalidity of U.S. Patent No. 5,843,497, Civ. No. 02-631 (JAG), Hon. Joseph A. Greenaway, Jr., United States District Court for the District of New Jersey, Newark Vicinage.
Agricultural Handbook No. 8-4, U.S. Department of Agriculture, Science and Education Administration, Revised Jun. 1979.
Archer Daniels Midland Company (Decatur, Il.), Soybean Oil, Product No. 86-070-0 (1997).
Berry, Shiv K., "Physico-chemical Characteristics of Palm Olein and Soybean Oil Blends," *Palm Oil Product Technology in the Eighties*, (1983) 483-498, The Incorporated Society of Planters, Kuala Lumpur.
Charnock et al., "Dietary modulation of lipid metabolism and mechanical performance of the heart", *3rd Intl. Symp. On Lipid Metabolism in the Normal and Ischemic Heart* (Sep. 9-10, 1991).
Choi et al., "Effect of dietary n-3 polyunsaturated fatty acids on cholesterol synthesis and degrdation in rats of different ages", *Lipids* 24(1):45-50 (1989).

Demacker et al., "Increased removal of remnants of triglyceride-rich lipoporiteins on a diet rich in polyunsaturated fatty acids", *European J. of Clin. Invest.* 21:197-203 (1991).

Firestone, David, "Physical and Chemical Characteristics of Oils, Fats and Waxes," (1999).

Formo, et al., *Bailey's Industrial Oil and Fat Products—vol. 1, Fourth Edition*, 379, John Wiley & Sons, New York.

Fujikawa, "Manufacture of Salad Oil", *Jpn. Kokai Tokkyo Koho JP* 61,293, 389 (86,293,389) (Dec. 26, 1986).

Grundy & Denke, "Dietary influences on serum lipids and lipoproteins", *J. Lipid Research* 31:1149-1172 (1990).

Grundy, "Comparison of monounsaturated fatty acids and carbohydrates for lowering plasma cholesterol", *N. Eng. J. Med.* 314:745-748 (1986).

Grundy, "Influence of stearic acid on cholesterol metabolism relative to other long-chain fatty acids", *American J. Clin. Nutr.* 60(suppl.):986S-990S (1994).

Haga, "Manufacture of Edible Oils," *Jpn. Kokai Tokkyo Koho JP*, 61,296,096 [86,296,096] (Dec. 26, 1986).

Han, Yoon-Sook, "Effect of Palm Oil Blending on the Thermal and Oxidative Stability of Soybean Oil," *Korean J. Food Sci. Technol.* 23(4):465-470 (1991).

Hayes, et al., "Dietary Saturated Fatty Acids (12:0, 14:0, 16:0) Differ In Their Impact On Plasma Cholesterol And Lipoproteins In Nonhuman Primates," *Am. J. Clin. Nutr.* 53:491-498 (1991).

Hayes, and Kholsa, "Dietary Fatty Acid Thresholds And Cholesterolemia," *FASEB* 6:2600-2607 (1992).

Hegsted, et al., "Quantitative Effects On Dietary Fat On Serum Cholesterol In Man," *Amer. J. of Clin. Nutr.* 17:281-295 (1965).

Hegsted, et al., "Dietary Fat And Serum Lipids: An Evaluation Of The Experimental Data," *Amm. J. of Clin. Nutr.* 57:875-883 (1993).

Heyden, "Polyunsaturated And Monounsaturated Fatty Acids In The Diet Prevent Coronary Heart Disease Via Cholesterol Reduction," *Ann. Nutr. Metab.* 38:117-122 (1994).

Hu, et al., "Dietary Fat Intake And The Risk Of Coronary Heart Disease In Woman," New England Journal Medicine, 337:1491-1499 (1997).

Jacobs, et al., "Variability In Individual Serum Cholesterol Response To Change In Diet," *Arteriosclerosis* 3:349-356 (1983).

Kajimoto, et al., "Influence Of Blend Ratio Of Vegetable Oils On Their Thermal Oxidation And Decomposition Of Tocopherol," *Nippon Eiyo, Shokuryo Gakkaishi* 44(6):499-505 (1991).

Katan, et al., "Effects Of Fats And Fatty Acids On Blood Lipids In Humans: An Overview 1-4," *Am. J. Clin. Nutr.* 60(Suppl):1017S-1022S (1994).

Khosla and Hayes, "Dietary Fat Saturation In Rhesuss Monkeys Affects LDL Concentrations By Modulating The Independent Production Of LDL Apolipoprotein B," *Biochem. Biophys. Acta* 1083:46-56 (1991).

Khosla and Hayes, "Comparison Between The Effects Of Dietary Saturated (16:0), Monounsaturated (18:1), and Polyunsaturated (18:2) Fatty Acids On Plasma Lipoprotein Metabolism In Cebus And Rhesus Monkeys Fed Cholesterol-Free Diets," *Am. J. Clin. Nutr.* 55:51-62 (1992).

Kifli, et al., "Physical Properties Of Interesterified Palm Oil/Palm Oil Fractions With Other Vegetable Oils," *Palm Oil. Prod. Techol. Eighties, Rep. Proc.* 303-314 (1981).

Kim, "Relationship Between The Triacylglycerol Composition And Foaming Of Mixed Coconut Oil Under Deep-Fat Frying," *Agric. Biol. Chem.* 52(3):693-699 (1988).

Lim, et al., "Oxidative Stability Of Malaysian Palm Oil And Its Blends," *Yukagaku* 39(12):1045-1049 (1990).

Litherland, et al., "Preparation Of Chocolate Fats By Wet Fractionation Of Soya Oil," *Abst. Of EP 428,200* (1991), *GB 89/25,943* (1989).

Majumdar, et al., "Vanaspati And Margarine Fat Base From Palm Oil And Palm Stearin By Corandomization With Cottonseed Oil," *J. Oil Techol. Assoc. India* 18(2):37-38 (1986).

Mensink and Katan, "Effect Of Dietary Fatty Acids On Serum Lipids And Lipoproteins," *Arteriosclerosis And Thrombosis* 12:911-919 (1992).

Murakami, et al., "Effect Of Processed Oils And Fats On Cholesterol Metabolism. IV. Effect Of Palm Stearin And Changes In Its Effect By Blending With Soybean Oil And Further Randomizing," *Yakagaku* 41(3):196-202 (1992).

Murakami, et al., "Effect Of Processed Oils And Fats On Cholesterol Metabolism. V. Effect Of Lard, Its Blend With Palm Olein And Their Randomized Oil," *Yukagaku* 41(7):530-537 (1992).

Pronczuk, et al., "Dietary Myristic, Palmitic, and Linoleic Acids Modulate Cholesterolemia In Gerbils," *FASEB J.* 8:1191-1200 (1994).

Reeves, James B. and Weihrauch, John L., "Composition of Foods Fats and Oils Raw Processed Prepared," *Agricultural Handbook No. 8-4* (1979) 1-142, Science and Education Administration U.S. Department of Agriculture, Washington, D.C.

Siguel and Maclure, "Relative Activity of Unsaturated Fatty Acid Metabolic Pathways In Humans," *Metabolism* 36:664-669 (1987).

*Spectrum Organic Products, Inc. v. GFA Brands, Inc. and Brandeis University*, First Amended Complaint for Declaratory Judgment of Non-Infringement and Invalidity of U.S. Patent No. 5,843,497, Civ. No. 02-631 (JAG), Hon. Joseph A. Greenaway, Jr., United States District Court for the District of New Jersey, Newark Vicinage.

Sundram, et al., "Dietary Plamitic Acid Results In Lower Serum Cholesterol Than Does A Lauric-Myristic Acid Combination in Normolipemic Humans,"*Am. J. Clin. Nutr.* 59:841-846 (1994).

Sundram, et al., Fat (Fatty Acid) Modulation Of Metabolism (2549-2554) *FASEB J.* 9:A440 (1995) (Abstract).

Suzuki, et al., "Fat And Oil Compositions For Frying And Spraying," *Jpn. Kokai Tokkyo Koho* JP 01,262,754 [89,262,754] (1989).

Swern, *Baileys Industrial Oil And Fat Products*, vol. 1, 4$^{th}$ Edition, John Wiley and Sons, New York, 311-332 and 363-368 (1979).

Wai, "A Critical Review Of The Cholesterolaemic Effects Of Palm Oil," *Food and Nutrition Bulletin* 15:112-123 (1994).

Willet and Sacks, "Chewing The Fat—How Much And What Kind," *N. Eng. J. of Med.* 324:121-123 (1991).

Wong et al., Fundamentals of Dairy Chemistry, Third Edition, 1988, Von Nostrand Rheinhold Company, New York, pp. 743-744.

Department of Health, Report on Health and Social Subjects, 41 Dietary Reference Values for Food Energy and Nutrients for the United Kingdom, HMSO, 1991, ISBN 0 11 321397 2, pp. iii-vi and 40-60.

Lindsey, et al., Dietary palmitic acid (16:0) enhances high density lipoprotein choleterol and low density lipoprotein receptor mRNA abundance in hamsters, Proceedings of the Society for Experimental Biology and Medicine, vol. 195, No. 2, Nov. 1990, pp. 261-269.

Lipid Handbook, Gunstone et al., Chapman and Hall Ltd. 1986, pp. 76-78 and 88-89.

Sundram, et al., Replacement of dietary fat with palm oil: effecT on human serum lipids, lipoproteins and apolopoproteins, British Journal of Nutrition (1992), 68, pp.677-692.

Sundram, et al., Characteristics of palm oil based food products developed for a nutritional intervention programme, Food Sciences and Nutrition (1990), 42F, pp. 193-202.

Sundram, et al., Both dietary 18:2 and 16:0 may be required to improve the serum LDL/HDL cholestorol ratio in normocholesterolemic men, Nutritional Biochemistry, (1995) 6:179-187.

Tan, et al., Novel fractions and fats from palm and palm kernel oils, Palm Oil Developments, 1989, vol. 11, pp. 18-23.

Fats and Oils, Unilever Educational Booklet: Advanced Series, Unilever Jan. 1994.

\* cited by examiner

INCREASING THE HDL LEVEL AND THE HDL/LDL RATIO IN HUMAN SERUM BY BALANCING SATURATED AND POLYUNSATURATED DIETARY FATTY ACIDS

RELATED APPLICATIONS

This application is a continuation of Perlman et al., U.S. application Ser. No. 09/828,448 filed Apr. 6, 2001, now U.S. Pat. No. 6,630,192 which is a continuation-in-part of Perlman et al., U.S. application Ser. No. 09/241,603, now abandoned, which is a continuation-in-part of Perlman et al., U.S. application Ser. No. 08/755,591 filed Nov. 25, 1996, now U.S. Pat. No. 5,874,117, which is a continuation-in-part of Perlman et al., U.S. application Ser. No. 08/626,461 filed Apr. 2, 1996, now U.S. Pat. No. 5,843,497, which is a continuation-in-part of U.S. application Ser. No. 08/41 8,641 filed Apr. 7, 1996, now U.S. Pat. No. 5,578,334, all of which are incorporated herein by reference in their entireties, including drawings.

BACKGROUND OF THE INVENTION

This invention relates to particular fats and fat blends, and methods for their manufacture or genetic selection/engineering, and use in foods. Consumption of such fats in appropriate amounts stabilizes or lowers the low density lipoprotein cholesterol (LDL or LDL-C) concentration and increases the high density lipoprotein cholesterol (HDL or HDL-C) concentration in human serum. This invention also relates to filled dairy products and to a method for preventing the development of off-flavors in these products.

The description and references herein are provided solely to assist the understanding of the reader. None of the information or references are admitted to be prior art to the present invention.

Coronary heart disease (CHD) is the major cause of death in the USA and other affluent nations. Plasma cholesterol, more specifically the LDL/HDL ratio, is highly correlated with risk of CHD as documented by Willett and Sacks, 324 N. Eng. J. Med. 121, 1991. The accumulation of LDL in the arterial intima is thought to lead to its oxidation, which in turn results in cascading events that induce arterial occlusion and thrombosis. High concentrations of HDL appear to block LDL oxidation and reduce the atherogenic potential of LDL. Thus, dietary means which decrease the LDL/HDL ratio (or increase the HDL/LDL ratio), especially means which would increase HDL, are desirable. Perlman and Hayes, U.S. Pat. No. 5,382,442 describe modified fat compositions and methods for decreasing total serum cholesterol while simultaneously decreasing the LDL/HDL serum cholesterol ratio. This ratio decreased as both the LDL and HDL concentrations decreased. The net LDL/HDL ratio in the serum decreased only because the LDL cholesterol concentration decreased by a greater factor than serum HDL with the dietary use of a fat-oil blend which included one to ten parts by weight cholesterol-reduced animal fat containing myristic acid, and one part by weight vegetable oil containing linoleic acid.

Within the past three years several authors have collected and analyzed a large number of independent metabolic studies relating to the effect of saturated, monounsaturated, and polyunsaturated fatty acids in the diet on serum LDL and HDL cholesterol levels. These studies have included the techniques of multiple regression analysis to examine LDL and HDL levels versus dietary intake of each group of fatty acids as separate variables expressed as the percentage of dietary energy, i.e., the total daily calorie intake of individuals in the studies.

Mensink and Katan (12 Arteriosclerosis and Thrombosis 911, 1992) made the following conclusions; "Replacement of saturated by unsaturated fatty acids raised the HDL to LDL cholesterol ratio, whereas replacement by carbohydrates had no effect. Thus, under isocaloric metabolic-ward conditions the most favorable lipoprotein risk profile for coronary heart disease was achieved if saturated fatty acids were replaced with unsaturated fatty acids, with no decrease in total fat intake." Hegsted et al. (57 Am. J. Clin. Nutr. 875, 1993), combined data from 155 human trials in which LDL and HDL cholesterol measurements were available. With regard to fatty acids and cholesterol in the diet, the authors state in their published abstract, "1) saturated fatty acids increase and are the primary determinants of serum cholesterol, 2) polyunsaturated fatty acids actively lower serum cholesterol, 3) monounsaturated fatty acids have no independent effect on serum cholesterol and 4) dietary cholesterol increases serum cholesterol and must be considered when the effects of fatty acids are evaluated. More limited data on low density lipoprotein cholesterol (LDL-C) show that changes in LDL-C roughly parallel the changes in serum cholesterol but that changes in high density lipoprotein cholesterol cannot be satisfactorily predicted from available data." Within this cited article, Hegsted et al. show that LDL levels increase an average of 1.74 mg/dl for each 1% increase in dietary energy represented by saturated fatty acids, while LDL levels decrease an average of 0.77 mg/dl for the corresponding amount of polyunsaturated fatty acids. Referring to the possibility of predicting changes in HDL levels in the serum, these same authors state, "It does not appear possible to develop an equation that predicts changes in HDL-C satisfactorily" and, "The errors in the regression coefficients are large; hence, little reliance should be placed on the equation." These authors calculate a very modest increase in HDL-C correlating with a dietary increase in either saturated or polyunsaturated fatty acids (0.43 mg/dl for a 1 increase in dietary energy represented by saturated fatty acids and 0.22 mg/dl for the corresponding amount of polyunsaturated fatty acids). This indicates that one would expect that for saturated fatty acids, the much smaller increase in HDL (0.43) versus LDL (1.74) per dietary energy, would typically result in a decrease in the HDL/LDL ratio as the saturated fatty acids are increased. On the other hand, the Hegsted et al. and the Mensink and Katan calculations would predict that an increase in the proportion of dietary polyunsaturated fatty acids at the expense of saturated fatty acids would increase the HDL/LDL ratio because this dietary increase caused a large decrease in LDL (approximately 2 mg/dl) and only a small proportional decrease in HDL (approximately 0.2 mg/dl). By comparison, the overall HDL/LDL serum ratios in these studies ranged from approximately 0.25 to 0.50.

Fat blends which include saturated vegetable fats in combination with polyunsaturated vegetable oils have been noted for dietary and/or cooking use. For example, Choi et al., 24(1) Lipids 45, 1989, describe cholesterol synthesis in rats with the feeding of safflower oil or linseed oil blended with palm olein in purified diets containing 10% fat. Suzuki et al.(Jpn. Kokai Tokkyo Koho JP 01, 262, 753>89, 262, 753! 19 Oct. 1989), describe the use of 40–90% natural palm oil and 60–5% natural vegetable oil in deep frying. Lim et al., (39(12) Yukagaku 1045, 1990) describe the increased oxidative stability of soybean oil blended with crude or refined palm oil or refined palm kernel oil. Murakami et al., (41 (3) Yukagahu 196, 1992) describe the feeding of soybean oil blended with an equal weight of palm stearin in diets containing 20% fat in which cholesterol metabolism was monitored in rats. Kajimoto et al., (44(6) Nippon Eiyo, Shokuryo Gakkaishi 499, 1991) describe the blending of soybean oil or rapeseed oil with palm oil, and the blending of soybean oil, rapeseed oil and palm oil to enhance the oxidative stabilities of the polyunsaturated oils. Han et al., (23 (4) Han'guk Sikp'um Kwahakhoechi 465, 1991) describe the stabilization of soybean oil against thermal and oxidative degradation by blending with an equal or greater proportion of palm oil.

The public awareness of an increased risk of cardiovascular disease associated with dietary consumption of substantial amounts of fats rich in saturated fatty acids and cholesterol has led to an overall reduction in fat intake and an increased demand for foods containing unsaturated rather than saturated fatty acids. A multiplicity of clinical studies have shown that when certain dietary levels of saturated fats are replaced by unsaturated fats, one's total serum cholesterol level decreases. Since the milkfat, i.e., butter in dairy products contains approximately 0.22%–0.25% by weight cholesterol, more than 60% saturated fatty acids, and only approximately 4% polyunsaturated fatty acids, health-conscious individuals often prefer to consume dairy products in which the milkfat content has been reduced, eliminated, or replaced with vegetable oil.

Liquid milks are divided into various product categories based upon their weight percentage fat contents. Regular whole milk contains approximately 3.25% milkfat. Based upon an 8 fluid ounce (244 g) serving size, this corresponds to 7.9–8 grams (abbreviated g) milkfat and 35 milligrams (abbreviated mg) cholesterol per serving A "reduced fat" product must contain no more than 75% of the fat present in the original product, while a "low fat" product must contain no more than 3 g fat per serving. Thus, for milk having a 244 g serving size, a 2% milkfat-containing milk is termed a reduced fat product, while a 1% milkfat-containing milk is termed a low fat milk. On the other hand, to meet the current definition of "skim", "non-fat", or "fat-free" milk (having a 245 g serving size), the milk must contain less than 0.2% by weight milkfat, i.e., less than 0.5 g per serving, and less than 5 mg cholesterol per serving.

Filled milk is defined as skim milk which has been enriched in fat content by addition of vegetable oil. The literature on filled dairy products includes both liquid products and dried products which are reconstituted by addition of water. A number of patents describe the substitution of vegetable oils for milkfat in filled milks, to obtain nutritionally improved products which are lower in saturated fat and cholesterol. However, these modified dairy products often have an altered or unnatural flavor and mouthfeel. Howard, U.S. Pat. No. 2,659,676, describes a dried milk product prepared from skim milk and palm fat. The vegetable fat and lecithin are added to heated skim milk, which is then pasteurized, homogenized and spray-dried. Stein et al., German Offenlegungsschrift 2,444,213, describes a dried milk containing a reduced proportion of saturated fat in which polyunsaturated fat is mixed with evaporated concentrated milk which is then homogenized and dried. Kneeland, U.S. Pat. No. 3,011,893, describes a reconstituted milk prepared from powdered skim milk, vegetable oil, and water, in which a mixture of the skim milk and water is heated, vegetable oil is added, and the mixture is homogenized and pasteurized. Bundus, U.S. Pat. No. 3,488,198, describes a filled milk prepared from skim milk solids, water, fat, and a water-in-oil emulsifier. The fat may be any one of a variety of vegetable fats and oils or hydrogenated vegetable oils including coconut oil, palm oil, cottonseed, corn, soybean, peanut, olive oil, and hydrogenated derivatives of several of these oils. Arndt, U.S. Pat. No. 3,843,828, describes a simulated milk product which includes vegetable protein, whey and hydrogenated vegetable oil. Bookwalter et al., U.S. Pat. No. 4,842,884, describes a milk concentrate prepared from nonfat dry milk and vegetable oil.

Vegetable oils are also used as vehicles for adding vitamins and minerals to fortify dairy products. For example, Karinen, U.S. Pat. No. 4,803,087, describes vitamin A and D fortification of milk using an aqueous emulsion of vegetable oil and an emulsifier.

In recent years, several patents have described the composition and preparation of improved flavor vegetable oil-containing filled milks which are asserted to possess the flavor and mouthfeel of whole milk. It is suggested that these filled milks are healthier than ordinary milk due to the absence of cholesterol and the significantly lower saturated fat content. For example, Arcadipane, U.S. Pat. No. 5,393,551, describes a filled milk having a butterfat substitute providing the taste and mouthfeel of an unmodified milk with the same amount of butterfat (ranging from 1% to 4%). The butterfat substitute includes 66%–98% of a partially hydrogenated soybean oil whose major fatty acids are present in approximately the following proportions: saturated fatty acids: palmitic 11%, stearic 14%; monounsaturated fatty acid: oleic 68%. A small proportion of the polyunsaturated fatty acids, linoleic 6%, and linolenic 0.1%, are also present. Arcadipane states that a filled milk assembled from skim milk, mono- and diglyceride emulsifiers, and the above partially hydrogenated soybean oil has an extended shelf life compared to ordinary milk, and may be stored under the same conditions as ordinary milk. While the pre-hydrogenated soybean oil contains approximately 63% polyunsaturated fat, this level is reduced to only 2% to 8% after hydrogenation. Strong et al., U.S. Pat. No. 5,580,600, describes a filled milk containing principally monounsaturated vegetable oil. A high oleic acid-containing vegetable oil such as rapeseed or sunflower oil containing at least 70% oleic acid, and no more than 12% by weight polyunsaturated linoleic acid and no more than 0.5% linolenic acid is combined with skim milk, an emulsifier, a polysaccharide modifier, and a carbohydrate gel stabilizer for the emulsion. Strong et al. states that a high proportion of oleic acid-rich vegetable oil is used to avoid the problems of rancidity and off-flavors which develop after relatively short periods of storage when a substantial proportion of the added vegetable oil is in the form of polyunsaturated fats and oils. Despite the rancidity problem associated with polyunsaturated vegetable oils, Kahn et al., U.S. Pat. No. 5,063,074, describes a low cholesterol, low fat, filled milk containing polyunsaturated vegetable oil, stated to have the taste and mouthfeel of whole or 2% milkfat-containing milk. The milk contains skim milk and 1%–5% of a premix (milkfat substitute) which includes 50%–70% non-tropical (polyunsaturated) vegetable oil such as soybean oil, 6%–10% of a non-lauric emulsifier, and a substantial proportion of flavoring agent (6%–10%) and food gum (15%–20%). The flavoring agent, which is a requirement of these milks, is most preferably 70%–90% natural milk distillate plus natural vanilla.

Light-induced alterations in the chemistry of conventional milkfat-based dairy products have been recognized and studied for many years. These alterations which, it has been suggested, may involve protein (amino acid) and lipid reactions, lead to the formation of taste changes which are invariably undesirable. When most dairy products, including regular milkfat-based milks, are stored under artificial lighting, e.g., fluorescent lighting, such flavor alterations occur gradually over the life of the product. The level of off-flavor development depends upon many factors including the type of lighting, product proximity to the light source, length of exposure and fat level of the milk. For example, regular milk containing 1% by weight milkfat, when stored in a translucent plastic jug, may show slight to moderate oxidized flavor development after 12 hours of typical retail fluorescent lighting exposure (200 footcandle exposure, see Example 2 below). Light can also destroy a number of important vitamins in milk with varying speed. Several light-susceptible vitamins include vitamin A (retinol), its provitamin, beta-carotene, vitamin $B_2$ (riboflavin) and vitamin C (ascorbic acid). The photosensitivity of vitamins A and $B_2$ in milk has been examined. The level of vitamin A in milk decreases rapidly upon exposure to visible (violet) light below a wavelength of 415 nm and to a lesser degree at wavelengths between 415 nm and 455 nm, while vitamin $B_2$ is degraded by light between the wavelengths of 415 nm and 455 nm (blue-violet). The rapidity of vitamin breakdown depends upon the intensity, duration and wavelength of light, the product storage temperature, and light transmittance through the product and its packaging. Skim milk, for example, is more transparent than regular milk (which contains emulsified fat), and its vitamins are therefore more susceptible to photodegradation.

Over the years, a variety of containers have been developed, which protect milks from the effects of natural and artificial light. These containers include printed paperboard cartons and pigmented and/or multi-layered plastic bottles. One such container is a white pigmented high density polyethylene (HDPE) jug recently brought to market by the H.P. Hood Company (Chelsea, Mass). Tests of the one gallon and half gallon sizes of this so-called "Light-Block Bottle™" have shown that they block at least 85% to 90% of incident light between the wavelengths of 300 nm and 700 nm. At 400 nm and below, these containers block essentially all light.

SUMMARY OF THE INVENTION

Applicant has determined that in the consumption of dietary fat (as natural triglycerides) it is beneficial to maintain a specific ratio of saturated fatty acids to polyunsaturated fatty acids (at least 0.5:1 but less than 2:1) in the absence of cholesterol. Particularly, it is useful to ingest an adequate proportion of saturated fatty acids contributed by a vegetable oil source such as palm oil, palm olein or its equivalent combined with polyunsaturated fatty acids contributed by a vegetable oil source such as canola oil or soybean oil. Thus, the present invention relates to the dietary use of a cholesterol-free composition in which a balanced proportion of at least one saturated fatty acid such as palmitic acid, myristic acid, and lauric acid is provided together with an approximately equal proportion of at least one polyunsaturated fatty acid such as linoleic acid in the dietary fat. This balanced proportion can be achieved with a mixture of two or more vegetable oils and/or vegetable fats. Alternatively, with recent advances in plant breeding and selection using conventional or genetic engineering methods, the ratio of saturated to polyunsaturated fatty acids provided by single plant species can be manipulated. Thus, in the near future, with suitable plant breeding and selection, a vegetable oil-bearing single plant species may provide, within the range described above, a balanced proportion of saturated and polyunsaturated fatty acids. Furthermore, such plant breeding can provide an enhanced level of alpha-linolenic acid in addition to linoleic acid. There are already a number of examples of successful plant breeding or varietal selection efforts which have led to commercial alternatives in choosing a particular vegetable oil. For example, with the species *Carthamus tinctotius* (safflower), vareties of oil are available with either high oleic acid (>70%) or high linoleic acid (>70%). With the species *Helianthus annuus* (sunflower) varieties of oil are available with either medium (<60%) or high (<60%) levels of linoleic acid. Likewise, canola oil (rapeseed) is available from different varietal sources of two species (*Brassica napus* and *B. campestris*) with erucic acid (22:1) contents from zero to forty percent (see Baily's Industrial Oil and Fat Products, Vol. 1, D. Swern, ed., Wiley and Sons, New York). Such a composition will increase HDL cholesterol and increase the HDL/LDL ratio (or decrease the LDL/HDL ratio) in the serum of mammals including humans and other primates. According to the present invention, a method is described for increasing the HDL/LDL ratio in human serum in which the HDL concentration increases while the LDL concentration remains essentially constant or decreases. Accordingly, when daily injested fat in the human diet is provided at a level such that it accounts for approximately 30% of the total dietary energy (as currently recommended by the nutritional research community), the saturated fatty acids including palmitic acid, or lauric and myristic acid must constitute between 20% and 40% by weight of the daily dietary fat, and the polyunsaturated fatty acids including linoleic acid must constitute between 15% and 40% by weight of this fat to maximize the serum HDL/LDL ratio. As one example, a cholesterol-free natural triglyceride fat blend containing equal proportions of approximately 30% by weight palmitic acid and 30% by weight linoleic acid plus linolenic acid is useful in the present invention. For this invention to be completely effective, it is important that certain cholesterolemic components be substantially absent from the diet. These components include but are not limited to dietary cholesterol and trans fatty acids, e.g., triglycerides containing elaidic acid produced during partial hydrogenation of vegetable oils. Illustrating this point with a human nutritional study, Sundram et al. (9 FASEB J. 000, 1995, Abstr.) have shown that exchanging trans 18:1 (elaidic acid) for cis 18:1 (oleic acid) caused a large increase in LDL and a decrease in HDL (where trans and cis 18:1 represented respectively, 7% and 16% of the dietary energy). This result and effect is opposite to the desired effect of the present invention.

Applicant has determined that a moderate proportion of saturated fatty acids is beneficial for increasing the HDL/LDL ratio in human serum and that a large proportion of polyunsaturated fatty acids in the dietary fat may, surprisingly, be undesirable in depressing this ratio.

Such advantages are achieved when the diet is essentially free of trans fats (e.g., elaidic) and represents the actual profile of fatty acid intake of the human.

Thus, in a first aspect, the invention features a method of increasing the HDL concentration and the HDL/LDL concentration ratio in human serum. This is achieved by providing a balance between a sufficient and required proportion of cholesterol-free saturated fatty acids in the daily dietary fat of a human, and a sufficient and required, but not excessive proportion of polyunsaturated fatty acids including linoleic acid in dietary fat. The remaining proportion of fatty acids and energy from dietary fat is provided by monounsaturated fatty acids including oleic acid. This means that the saturated fatty acids constitutes between 20% and 40% by weight of the daily dietary fat (based upon dietary fat accounting for 30% of the total dietary energy consumption). It also means that linoleic acid constitutes between 15% and 40% by weight of this dietary fat. These constituents will provide the required proportional intake of polyunsaturated fatty acids and thereby enhance the formation of HDL from VLDL and/or decrease the clearance of HDL. An excessive proportional intake of polyunsaturated fatty acids and monounsaturated fatty acids is also avoided in such a formulation to assure a sufficient dietary availability of saturated fatty acids which are required for sufficient VLDL synthesis and HDL production. Such a dietary fat composition is consistent with the dietary fat composition of the Step I diet of the American Heart Association.

In preferred embodiments, the cholesterol-free saturated fatty acids include palmitic acid, lauric acid and myristic acid; the proportion of monounsaturated fatty acids in the daily dietary fat is between 20% and 50% oleic acid and no greater than 1% elaidic acid (or other unnatural trans fatty acids) by weight; the polyunsaturated fatty acids include linoleic acid and at least one other polyunsaturated fatty acid selected from the group including alpha-linolenic acid, eicosapentenoic acid (EPA), and docosahexenoic acid (DHA); and the proportion of saturated fatty acids in the daily dietary fat is at least 20% by weight and dietary fat has less than 5% by weight stearic acid.

In a second related aspect, the invention features a method of stabilizing or decreasing the LDL concentration in human serum by providing saturated fatty acids in the daily diet in a proportion between 20% and 40% by weight of the daily dietary fat (based upon dietary fat accounting for 30% of the total dietary energy consumption), and maintaining a proportion of polyunsaturated fatty acids (including linoleic acid) in the daily diet at the expense of monounsaturated fatty acids (including oleic acid and/or elaidic acid). The linoleic acid constitutes between 15% and 40% by weight of dietary fat. Removal of plasma VLDL remnants and LDL is maximized by this formulation, and the production of LDL is reduced.

In a third related aspect, the invention features a method of increasing the HDL and stabilizing or decreasing the LDL concentration in human serum by providing saturated fatty acids in the daily diet in a proportion between 20% and 40% by weight of the daily dietary fat (based upon dietary fat accounting for 30% of the total dietary energy consumption), whereby the production of VLDL, as the HDL precursor, is adequately sustained and is not limiting in HDL biosynthesis. In addition, the method includes maintaining a proportion of polyunsaturated fatty acids (including linoleic acid) in the daily diet at the expense of monounsaturated fatty acids (including oleic acid and/or elaidic acid), wherein linoleic acid constitutes between 15% and 40% by weight of dietary fat, whereby VLDL catabolism to HDL is facilitated and hepatic clearance of VLDL remnants and LDL is enhanced.

In a fourth related aspect, the invention features a method of increasing the HDL concentration and the HDL/LDL concentration ratio in human serum by the dietary consumption of foods prepared using a cholesterol-free single fat composition or blended fat composition containing a ratio of one part by weight polyunsaturated fatty acids to at least one part by weight saturated fatty acids. The single fat composition or blended fat composition includes linoleic acid and at least one saturated fatty acid selected from the group including lauric acid, myristic acid, and palmitic acid. The linoleic acid constitutes between 15% by weight and 40% by weight of the composition and saturated fatty acid constitutes between 20% and 40% by weight of the composition. In this way, adequate dietary levels of saturated fatty acids in the absence of cholesterol stimulate VLDL synthesis and secretion by the liver, and adequate dietary levels of linoleic acid enhance LPL activity and generation of HDL from VLDL while stimulating the removal of VLDL remnants and LDL, and concommitently decreasing CETP activity and HDL catabolism.

In preferred embodiments of the above aspects, the food-source of saturated fatty acids includes at least one vegetable fat selected from the group including palm fat, coconut fat and cocoa butter; the palm fat is selected from the group including palm oil, palm olein, and palm kernel oil; the food source of polyunsaturated fatty acids includes at least one vegetable oil selected from the group including corn oil, sunflower oil, safflower oil, soybean oil, cottonseed oil, canola oil, and peanut oil; alternatively, the food source of both saturated fatty acids and polyunsaturated fatty acids is a single vegetable oil species which has been selected or engineered to provide the requisite balance of saturated and polyunsaturated fatty acids; the polyunsaturated fatty acids include linoleic acid and linolenic acid; wherein linolenic acid is contributed by soybean oil, canola oil, edible flax seed oil, and/or perrilla seed oil; within the single fat composition or blended fat composition is provided a proportion of at least one part by weight cholesterol-free saturated fat to one part by weight polyunsaturated fat to stabilize the polyunsaturated fat against oxidation; the oxidation-resistance of the single fat or blended fat composition upon heating to a temperature of 100.degree. C. or greater in air is increased by at least 25% compared to the oxidation resistance of the polyunsaturated fat component when heated separately from the single fat or blended fat composition; essentially all of dietary fat is provided in a nutritionally balanced liquid and/or solid formula diet in which dietary fat accounts for between 15% and 45% of the total dietary energy consumption; the dietary fat accounts for between 20% and 30% of the total dietary energy consumption; the compositions noted above are used in place of dietary consumption of foods prepared using a blended fat composition, that is, such foods are substituted with the dietary consumption of a nutritionally balanced liquid formula diet prepared using a single fat or blended fat composition in which the total fat content therein accounts for between 15% and 45% of the total dietary energy consumption; daily dietary fat or foods contain a blended fat composition including one part by weight of at least one polyunsaturated vegetable oil selected from the group including corn oil, sunflower oil, safflower oil, soybean oil, cottonseed oil, canola oil, and peanut oil blended with at least one part by weight of vegetable fat including saturated fatty acids; the vegetable fat is selected from the group including palm fat, coconut fat and cocoa butter; and the palm fat is selected from the group including palm oil, palm olein, and palm kernel oil. Alternatively the daily dietary fat or foods contain a single vegetable oil species which has been selected or engineered to provide the requisite balance of saturated and polyunsaturated fatty acids.

In a fourth related aspect, the invention features a method of increasing the HDL concentration and the HDL/LDL concentration ratio in human serum by the dietary consumption of foods. These foods are prepared using at least one modified fat selected from the group including a chemically interesterified fat, an enzymatically interesterified fat, and a synthetic fat. The modified fat includes one part by weight polyunsaturated fatty acids and at least one part by weight saturated fatty acids selected from the group including lauric acid, myristic acid, and palmitic acid. The polyunsaturated fatty acids constitute between 15% by weight and 40% by weight of modified fat, and the saturated fatty acids constitute between 20% and 40% by weight of modified fat. In this way adequate dietary levels of saturated fatty acids in the absence of cholesterol stimulate VLDL synthesis and secretion by the liver, and adequate dietary levels of polyunsaturated fatty acids enhance LPL activity and generation of HDL from VLDL while stimulating the removal of VLDL remnants and LDL and concommitently decreasing CETP activity and HDL catabolism (FIG. 1).

Preferably, the weight ratio of saturated fatty acids to polyunsaturated fatty acids included in dietary fat, modified fat, or blended fat composition ranges from 0.5:1.0 to 2.0:1.0; and the weight ratio is approximately (±20%) 1 to 1.

In a fifth related aspect, the invention features a liquid and/or solid dietary composition suitable for human or animal ingestion for increasing the HDL concentration and the HDL/LDL concentration ratio in the blood serum. Essentially all of dietary fat which accounts for between 15% and 45% of the total dietary energy in liquid formula diet, is provided by a single fat or a blended fat composition containing one part by weight polyunsaturated fat and at least one part by weight cholesterol-free saturated fat. The single fat or blended fat composition includes linoleic acid and at least one saturated fatty acid selected from the group including lauric acid, myristic acid, and palmitic acid. The linoleic acid constitutes between 15% by weight and 40% by weight of the composition, and saturated fatty acid constitutes between 20% and 40% by weight of composition.

In preferred embodiments, dietary fat accounts for between 20% and 30% of the total dietary energy in the liquid formula diet; the saturated fatty acid is predominantly palmitic acid; and a reduction in cardiac arrythmia accompanies the increase in HDL concentration and the increase in HDL/LDL concentration ratio.

Suitable sources for cholesterol-free fats containing saturated fatty acids include saturated vegetable fats such as palm fat, coconut fat, and cocoa butter. Palm oil, palm olein, and palm kernel oil are particularly useful sources for the saturated fatty acids. Suitable sources for polyunsaturated fatty acids include the vegetable oils which are rich in linoleic acid such as corn oil, sunflower oil, safflower oil, soybean oil, and cottonseed oil for example. The above-mentioned vegetable fats and oils can be blended in appropriate ratios according to the content of the above-mentioned saturated and polyunsaturated fatty acids therein, to produce dietary fat blends having the recommended proportions by weight of saturated and polyunsaturated fatty acids (see Tables I and II for the fatty acid content of various vegetable fats and oils as derived from published data >Agriculture Handbook No. 8-4, U.S.D.A. Science and Education Administration, Composition of Foods: Fats and Oils!).

TABLE I

Polyunsaturated Vegetable Oils

|  | Safflower | Sunflower | Corn | Cottonseed | Soybean | Peanut | Canola |
|---|---|---|---|---|---|---|---|
| SATs (wt %) | | | | | | | |
| Total | 9.1 | 10.3 | 12.7 | 25.9 | 14.4 | 16.9 | 7.1 |
| 14:0 | 0.1 | | | 0.8 | 0.1 | 0.1 | |

TABLE I-continued

Polyunsaturated Vegetable Oils

|  | Safflower | Sunflower | Corn | Cottonseed | Soybean | Peanut | Canola |
|---|---|---|---|---|---|---|---|
| 16:0 | 6.2 | 5.9 | 10.9 | 22.7 | 10.3 | 9.5 | 4.0 |
| 18:0 | 2.2 | 4.5 | 1.8 | 2.3 | 3.8 | 2.2 | 1.8 |
| MONOs (wt %) | | | | | | | |
| Total | 12.1 | 19.5 | 24.2 | 17.8 | 23.3 | 46.2 | 58.9 |
| 18:1 | 11.7 | 19.5 | 24.2 | 17.0 | 22.8 | 44.8 | 56.1 |
| 20:1 | | | | | 0.2 | 1.3 | 1.7 |
| POLYs (wt %) | | | | | | | |
| Total | 74.5 | 65.7 | 58.7 | 51.9 | 57.9 | 32.0 | 29.6 |
| 18:2 | 74.1 | 65.7 | 58.0 | 51.5 | 51.0 | 32.0 | 20.3 |
| 18:3 | 0.4 | | 0.7 | 0.2 | 6.8 | | 9.3 |

TABLE II

Saturated Vegetable Oils

|  | Coconut Oil | Cocoa Butter | Palm Oil | Palm Olein | Palm Kernel Oil |
|---|---|---|---|---|---|
| SATs (wt %) | | | | | |
| Total | 86.5 | 59.7 | 49.3 | 43.7 | 81.4 |
| 12.0 | 44.6 | | | | 47.0 |
| 14:0 | 16.8 | 0.1 | 1.0 | 0.8 | 16.4 |
| 16:0 | 8.2 | 25.4 | 43.5 | 38.9 | 8.1 |
| 18:0 | 2.8 | 33.2 | 4.3 | 4.0 | 2.8 |
| MONOs (wt %) | | | | | |
| Total | 5.8 | 32.9 | 37.0 | 45.0 | 11.4 |
| 18:1 | 5.8 | 32.9 | 36.6 | 45.0 | 11.4 |
| 20:1 | | | 0.1 | | |
| POLYs (wt %) | | | | | |
| Total | 1.8 | 3.0 | 9.3 | 11.3 | 1.6 |
| 18:2 | 1.8 | 2.8 | 9.1 | 10.9 | 1.6 |
| 18:3 | | 0.1 | 0.2 | 0.4 | |

For example, two parts palm oil (44% palmitic acid, 9% linoleic acid) can be blended with one part corn oil (11% palmitic acid, 58% linoleic acid) to provide a balanced fat blend containing approximately 33% palmitic acid (16:0) and 25% linoleic acid (18:2). Such cholesterol-free balanced fat blends are useful not only as dietary constituents that modulate plasma cholesterol to maximize the HDL/LDL ratio but also provide advantageous use in various cooking procedures such as in deep-fat frying. The fat blends may also be used in shortening for baked prepared foods (including cakes, pies, cookies, crackers, etc.), in dairy products (including frozen desserts, creams, cheeses, spreads), and in blended food products (including salad dressing, margarines, mayonnaise). In addition the fat blends may be used in liquid and/or solid dietary compositions for managing and controlling food intake such as for weight loss, control of hypercholesterolemia, or for managing any one of a variety of health conditions requiring a controlled diet in which the proportion and composition of the dietary fat must be controlled. As a practical matter, the balanced mixture of saturated and polyunsaturated fatty acids can be provided not only as a natural blend of cholesterol-free saturated fats and polyunsaturated oils, but also as a mixed fatty acid composition in the form of one or more modified or synthetic fats incorporating chemically or enzymatically interesterified fatty acids to achieve the balanced proportion of saturated and polyunsaturated fatty acids described in this invention.

The present invention also relates to a filled dairy product, such as milk, containing an emulsified polyunsaturated vegetable oil together with milkfat, where the fats are present in specified percentage ranges, and in which the product is substantially free of any flavoring agent. Compared to simple milkfat-based dairy products, the fat component of the filled dairy product contains a substantially increased proportion of polyunsaturated fatty acids and a substantially decreased proportion of saturated fatty acids and cholesterol. The invention also involves reducing or eliminating off-flavors which develop when polyunsaturated vegetable oils are emulsified into these dairy products, by excluding more than 90% of ambient visible light from the dairy products.

It has been shown that a pre-mix containing milkfat (or a cream rich in milkfat), plus a polyunsaturated vegetable oil (such as soybean oil) plus an effective amount of emulsifier (such as mono- and diglycerides), can be dispersed into skim milk (or reduced fat milk, or regular milk), and then pasteurized, homogenized and appropriately packaged in an opaque container. Suitable light-opaque packaging is used to achieve an adequate shelf-life and to sustain fresh taste in these filled dairy products. This discovery was surprising because Applicants expected that addition of the fat-soluble antioxidant, vitamin E, to the milk would protect the milk with its polyunsaturated fatty acids against air oxidation and off-flavor development. From the prior art, it was also anticipated that the addition of a suitable antioxidant (such as BHA, BHT, TBHQ or tocopherol) would protect the filled dairy products. Instead, it was found that vitamin E addition was of little help, while light exclusion was of great help. Simply stated, photochemical change in a polyunsaturated fat-filled dairy product appears to be the predominant source of off-flavors, and the "first line of defense" for these products must be light-excluding packaging (see Examples below).

The problem of development of off-flavors in filled milk products has been recognized (e.g., Strong et al., U.S. Pat. No. 5,580,600) and has resulted in the absence of such products in the market, and apparently discouraged development in this area. While the existence of the problem was acknowledged, neither the source of the problem, nor a solution directed to that source were shown. Instead, filled milk products utilized replacement fats which were more resistant to the development of off-flavors than polyunsaturated fats (e.g., monounsaturated vegetable oils or partially hydrogenated vegetable oils) or utilized flavor additives which would mask the development of off-flavors (e.g., milk distillate plus vanilla).

In contrast, for the present invention, photochemical changes in filled dairy products containing polyunsaturated vegetable oils were found to be at least a major, and apparently a predominant, factor in the development of off-flavors. It was further found that flavor stability could be maintained by preventing substantial exposure of the filled dairy product to light, particularly to visible wavelengths of light. By limiting or preventing exposure to visible light, it became practical to produce filled milk products which included a high proportion of polyunsaturated fats without the need to include a flavoring agent to mask the development of off-flavors.

It was also found that a filled milk product (or other filled dairy product) containing a substantial proportion of polyunsaturated vegetable oil could be produced, in which the balance between saturated fats and polyunsaturated fats is consistent with the ranges recommended in Sundram et al., U.S. Pat. No. 5,578,334 and Sundram et al, U.S. Pat. No. 5,843,497, which are hereby incorporated by reference in their entireties, including drawings. Those ranges were shown to sustain or enhance the HDL/LDL ratio in humans who ingested a diet with such a fat balance, preferably when cholesterolemic components such as elaidic acid were limited. It was further found that such a dairy product provided good taste and mouthfeel (much like regular milk) and that the taste could be preserved by limiting light exposure. As a result, it is practical to provide such milk or dairy products for general distribution.

Thus, the invention features a polyunsaturated vegetable oil-filled dairy product substantially free of any flavoring agent, in which the fat portion of the dairy product includes at least one polyunsaturated vegetable oil and milkfat. The fat portion includes between 15% and 40% by weight linoleic acid, between approximately 20% and 40% by weight saturated fatty acids, and no more than 1% by weight elaidic acid or other unnatural trans fatty acids. The fat portion and the aqueous portion of the dairy product constitute a stable emulsion. Generally the stable emulsion is provided by utilizing an effective concentration of at least one emulsifier capable of maintaining the vegetable oil and the milkfat as a stable emulsion in the dairy product. Flavor stability is provided by excluding or limiting exposure of the filled dairy product to visible light.

In preferred embodiments, the weight ratio of vegetable oil to milkfat in the fat portion of the filled dairy product is between approximately 2:1 and 1:2, preferably between 1.5:1 and 1:1.5. In preferred embodiments, the fat portion of the filled dairy product contains between approximately 20% and 40% by weight saturated fatty acids selected from the group consisting of palmitic acid, myristic acid, lauric acid, stearic acid, and combinations thereof.

In preferred embodiments, the dairy product is contained within a substantially light-opaque container which is used to exclude between 90% and 100% of visible light between the wavelengths of 300 nm and 700 nm which is incident upon the container, and the dairy product thereby can retain acceptable flavor after the container has received at least 24 hours cumulative exposure to at least 200 footcandles illumination at a temperature of 38° F. Illumination is typically in the form of artificial lighting, e.g., fluorescent lighting tubes, using warm white, cool white or some combination of these well known fluorescent lighting sources. The dairy product is placed in a substantially light-opaque container, in which the walls of the container are preferably fabricated from a material selected from the group consisting of opaque paperboard, pigmented thermoplastic resin and combinations thereof.

"Acceptable flavor" means that the filled dairy product does not have a level of development of off-flavors as to render the product unsuitable for general consumption by humans. This can be demonstrated by taste-testing using a panel of individuals, or preferably using at least two expert taste testers as in Example 2 below, where the average score on the described 1 to 5 scale is at least 4, preferably at least 4.5.

The term "substantially light opaque" means that at least 90% of the incident light is blocked, preferably at least 95%, more preferably at least 98%, and most preferably at least 99%.

In preferred embodiments, the fat portion of the filled dairy product further includes between 0.2% by weight and 10% by weight of the polyunsaturated fatty acid, linolenic acid; the cholesterol content of the filled dairy product is preferably reduced by at least 25% compared to a dairy product containing the same percentage by weight of fat which is limited solely to regular milkfat, i.e., unmodified milkfat; the filled dairy product is a filled milk which contains between 0.2% by weight and 20% by weight of at least one milkfat selected from the group consisting of regular milkfat and cholesterol-reduced milkfat; the cholesterol-reduced milkfat contains less than 10% of its original cholesterol content; the polyunsaturated vegetable oil is selected from the group consisting of soybean oil, corn oil, cottonseed oil, canola oil, sunflower oil, safflower oil, peanut oil and combinations thereof; the emulsifier includes a mixture of mono- and di-glycerides. The mono- and di-glycerides are preferably selected from the group consisting of glyceryl mono- and di-stearates, glyceryl mono- and di-oleates and combinations thereof.

In preferred embodiments, the filled dairy product is a filled milk product which, upon analysis or fractionation, includes between 55% and 99% by weight skim milk, between approximately 0.4% and 20% by weight of polyunsaturated vegetable oil, between approximately 0.4% by weight and 20% by weight of milkfat, and between approximately 0.1% and 5% of emulsifier; the filled dairy product is selected from the group consisting of filled milk, filled butter milk, filled cream, filled yogurt, filled sour cream, filled egg nog, filled ice cream, filled cottage cheese and filled cheese; the content of fat in the filled dairy product is selected from the group consisting of full fat content, reduced fat content and low fat content.

In a related aspect, the invention features a polyunsaturated vegetable oil-filled milk substantially free of any flavoring agent, as described for the filled dairy product of the aspect above. As in the above aspect, flavor stability is provided by excluding or limiting exposure to visible light. The filled milk includes a combination of skim milk and a substitute fat, in which the substitute fat contains at least 20% less saturated fat and cholesterol than would the same amount of regular milkfat. The substitute fat includes a combination of at least one polyunsaturated vegetable oil and milkfat, in which the substitute fat contains between 15% and 40% by weight linoleic acid, between approximately 20% and 40% by weight saturated fatty acids, and no more than 1% by weight elaidic acid or other unnatural trans fatty acids. The substitute fat and the aqueous portion are prepared as a stable emulsion. As in the aspect above, generally preparation of the stable emulsion involves inclusion of an effective amount of emulsifier capable of maintaining the combination of vegetable oil and milkfat as a stable emulsion.

In preferred embodiments, the polyunsaturated vegetable oil in the filled dairy product is selected from the group consisting of soybean oil, corn oil, cottonseed oil, canola oil, sunflower oil, safflower oil, peanut oil and combinations thereof. Preferred embodiments are also as described for the aspect above. In addition, as described in Sundram et al., U.S. Pat. No. 5,843,497, in this aspect and other aspects of this invention, a vegetable oil may be or include a genetically-engineered vegetable oil, and/or a modified or synthetic fat incorporating enzymatically or chemically interesterified fatty acids.

In another related aspect, the invention provides a filled dairy product substantially free of any flavoring agent. Again, flavor stability is provided by excluding or limiting exposure to visible light. The filled dairy product contains a substitute fat which includes milkfat and at least one polyunsaturated vegetable oil in a weight ratio ranging from approximately 1:2 to approximately 2:1. The substitute fat portion of the filled dairy product contains between 15% and 40% by weight linoleic acid, between approximately 15% and 40% by weight saturated fatty acids, and no more than 1% by weight elaidic acid or other unnatural trans fatty acids. The substitute fat and the aqueous portion form a stable emulsion. As indicated above, generally provision of the stable emulsion involves inclusion of an effective concentration of at least one emulsifier capable of maintaining the substitute fat as a stable emulsion in the dairy product.

In preferred embodiments, the polyunsaturated vegetable oil in the filled dairy product is selected from the group consisting of soybean oil, corn oil, cottonseed oil, canola oil, sunflower oil, safflower oil, peanut oil and combinations thereof. Preferred embodiments are also as described for the first aspect above.

In another aspect, the invention features a method of reducing or preventing development of off-flavors in a polyunsaturated vegetable oil-containing filled dairy product, and thereby obviating the need for including any flavoring agent. The method includes packaging the filled dairy product in a substantially light-opaque container excluding between 90% and 100% of visible light between the wavelengths of 300 nm and 700 nm which is incident upon the container, and limiting the intensity of the visible light entering the filled dairy product to between zero and 40 footcandles during multi-hour storage of the filled dairy product. The filled dairy product includes at least one polyunsaturated vegetable oil and milkfat, and is provided as a stable emulsion, e.g., by utilizing an effective concentration of at least one emulsifier capable of maintaining the vegetable oil and the milkfat as a stable emulsion in the filled dairy product.

In preferred embodiments of the method, the fat portion of the filled dairy product, which includes polyunsaturated vegetable oil and milkfat, contains between 15% and 40% by weight linoleic acid, between approximately 20% and 40% by weight saturated fatty acids, and no more than 1% by weight elaidic acid or other unnatural trans fatty acids.

Additional preferred embodiments include components as described for the first aspect above. Thus, in preferred embodiments of the method, the weight ratio of vegetable oil to milkfat in the fat portion of the filled dairy product is between approximately 2:1 and 1:2, preferably between 1.5:1 and 1:1.5.

In preferred embodiments of the method, the fat portion of the filled dairy product which includes milkfat, contains between approximately 20% and 40% by weight saturated fatty acids selected from the group consisting of palmitic acid, myristic acid, lauric acid, stearic acid, and combinations thereof.

In preferred embodiments of the method, the dairy product retains acceptable flavor after the exterior surface of the container has been cumulatively exposed to at least 200 footcandles illumination at a temperature of 38° F. for up to 14 days. The walls of the container are preferably fabricated from a material selected from the group consisting of opaque paperboard, pigmented thermoplastic resin and combinations thereof.

In other preferred embodiments of the method, the fat portion of the filled dairy product further includes between 0.2% by weight and 10% by weight linolenic acid. Among the vegetable oils, soybean oil is relatively rich in linolenic acid, the triply unsaturated eighteen carbon essential fatty acid (18:3). Also in preferred embodiments, the cholesterol content is reduced by at least 25% compared to a dairy product containing the same percentage by weight of fat which is limited solely to regular milkfat; the dairy product is a filled milk which includes between 0.2% by weight and 20% by weight of at least one milkfat selected from the group consisting of regular milkfat and cholesterol-reduced milkfat; the cholesterol-reduced milkfat contains less than 10% of its original cholesterol content; the polyunsaturated vegetable oil is selected from the group consisting of soybean oil, corn oil, cottonseed oil, canola oil, sunflower oil, safflower oil, peanut oil and combinations thereof; the emulsifier includes a mixture of mono- and di-glycerides, and preferably the mono- and di-glycerides are selected from the group consisting of glyceryl mono- and di-stearates, glyceryl mono- and di-oleates and combinations thereof; the dairy product is a filled milk product which, upon analysis or fractionation, comprises between 55% and 99% by weight skim milk, between approximately 0.4% and 20% by weight of polyunsaturated vegetable oil, between approximately 0.4% by weight and 20% by weight of milkfat, and between approximately 0.1% and 5% of emulsifier; the dairy product is selected from the group consisting of filled milk, filled butter milk, filled cream, filled yogurt, filled sour cream, filled egg nog, filled ice cream, filled cottage cheese and filled cheese; the content of fat in the dairy product is selected from the group consisting of full fat content, reduced fat content and low fat content dairy products.

In still another aspect, the invention features a method of substantially reducing the rate of development of off-flavors in a polyunsaturated vegetable oil-filled milk, and thereby obviating the need for including any flavoring agent therein. The filled milk is packaged in a substantially light-opaque container, preferably excluding at least 90% of visible light between the wavelengths of 300 nm and 700 nm which is incident upon the container. The intensity of the visible light entering the filled milk is limited to less than 40 footcandles during multi-hour storage of the filled milk. The fat portion of the filled milk contains between 15% and 40% by weight linoleic acid, between approximately 20% and 40% by weight saturated fatty acids, no more than 1% by weight elaidic acid or other unnatural trans fatty acids, and at least 25% less cholesterol than regular milkfat on a weight percentage basis. The filled milk is prepared as a stable emulsion, e.g., by including an effective concentration of at least one emulsifier capable of maintaining the vegetable oil and the milkfat as a stable emulsion in the filled milk.

In preferred embodiments of this method, the fat portion of the filled milk includes milkfat and at least one polyunsaturated vegetable oil in a weight ratio ranging from approximately 1:2 to approximately 2:1; the polyunsaturated vegetable oil is selected from the group consisting of soybean oil, corn oil, cottonseed oil, canola oil, sunflower oil, safflower oil, peanut oil and combinations thereof.

For the purposes of this invention, the following terms have the following definitions or meanings in context. The term "filled dairy product" refers to a milk-containing product which contains milk which is enriched in fat content by the addition of vegetable oils. Generally, a skim milk will be used, to which will be added a fat-containing component.

The term "substantially free", in the context of describing the presence of flavoring agent, differentiates the present compositions from compositions in which an added flavoring component or components is needed to mask off-flavors in the base dairy product, e.g., in a filled milk such as in Kahn et al., U.S. Pat. No. 5,063,074, in which a flavoring agent must be added. Thus, "substantially free" means that no flavoring agent is added into the basic filled dairy product to provide a flavor-stable product having the taste and mouthfeel of a dairy product having the same total fat content as milkfat only (rather than polyunsaturated vegetable oil plus milkfat). However, this term is not meant to prevent a manufacturer from adding ingredients to produce derivative dairy products such as fruit yogurts, which differ in flavor from the original or basic dairy products.

The term "flavor stability" is defined as maintaining a constant and high quality flavor (a score of at least 4 points, preferably at least 4.5 points, more preferably 5 points) over at least 14 days refrigeration at 38° F., as monitored and scored by at least two (or 3, 4, 5, or more) professional dairy product tasters (see Example 2).

The term "reduced proportion" in the context of saturated fat and cholesterol content means that there is at least a 20% reduction, and preferably a 25% reduction in the concentration (percentage by weight) of these materials in the product. More preferably the reduction is 50%, 75%, 90%, or more.

The term "polyunsaturated vegetable oil" refers to natural vegetable oils which are typically refined and deodorized, and preferably retain their natural triglyceride structure, rather than being either chemically modified, e.g., by interesterification, or by hydrogenation to reduce their content of esterified linoleic and linolenic fatty acids (polyunsaturated fatty acids). If modified, the polyunsaturated vegetable oil preferably contains less than 1% by weight elaidic acid or other unnatural trans fatty acids. A non-exclusive list of the common polyunsaturated vegetable oils includes soybean oil, corn oil, cottonseed oil, canola oil, sunflower oil, safflower oil and peanut oil. The polyunsaturated vegetable oils contain more than 25% by weight of linoleic acid plus linolenic acid. By contrast, certain vegetable oils including palm oil and coconut oil are considered saturated fats, containing at least 35% by weight saturated fatty acids such as palmitic and stearic acids, and less than 20% by weight polyunsaturated fatty acids. Anhydrous milkfat is a highly saturated fat, containing more than 60% saturated fatty acids, less than 30% monounsaturated fatty acid (oleic acid), and less than 5% polyunsaturated fatty acid (linoleic acid). Regular milkfat, i.e., butter contains approximately 16% water. Consequently, its fatty acid content is slightly lower, i.e., approximately 51% by weight saturated fatty acids, 23% monounsaturated fatty acids, and 3% polyunsaturated fatty acids.

The term "stable emulsion" in the context of the present invention means that the fat component of the filled dairy product (such as filled milk) does not physically separate to form a second liquid phase during the lifetime, i.e., shelflife, of the product. Thus, the absence of such a second liquid phase preferably persists for at least 1 week, more preferably at least 1½ weeks or 2 weeks, still more preferably at least 2½ or 3 weeks, and most preferably 4 weeks or longer. Usually, the formation and/or maintenance of the stable emulsion involves the incorporation of an adequate concentration (also termed an "effective concentration") of a food additive which aids in preventing separation of fats from the aqueous phase, e.g., an FDA approved, food grade emulsifier such as the mono- and diglycerides of stearic acid, oleic acid, and combinations thereof. In milk-type products, the stable emulsion is an oil-in-water type emulsion, meaning that microscopic droplets of milkfat and/or oil are dispersed as the internal phase, and the aqueous milk is the external phase.

The term "fat portion" in connection with a dairy product refers collectively to all fats and oils in the product, including, for example, milkfat and/or vegetable oils, along with any additional components solubilized or suspended in an oil phase. Such an oil phase may, for example, be an oil droplet or droplets of an oil-in-water emulsion. Similarly, the term "aqueous portion" refers to the water (i.e., aqueous) component along with non-fat and non-oil components solubilized or suspended in the water. Thus, for example, such components can include water-soluble proteins and mineral ions.

The term "light-opaque" in the context of a container which is suitable for protecting the filled dairy products, excludes at least 90% of visible light (between the wavelengths of 300 nm and 700 nm) which is incident upon the container, and preferably 95%, 98%, 99%, or more. The term "photodegradation" is used to describe chemical damage to the filled dairy product resulting from the action of light upon the product. As a process, it includes but is not limited to photooxidation. Photooxidation as a process requiring both oxygen and light energy input, is distinct from simple oxidation, which can occur in the dark. Opaque packaging material, rather than oxygen-excluding packaging, is used in the present invention because the former is inexpensive and has been shown to be effective in preventing development of off-flavors in the polyunsaturated fatty acid-filled products of the present invention. Moreover, opaque packaging will prevent all forms of photodegradation (including photooxidation), and such packaging is less expensive and more practical than packaging to exclude oxygen over the lifetime of the dairy product.

The term "artificial bright light storage" refers to typical lighting conditions used in the commercial retailing of dairy products. While incandescent illumination is included in this term, most retail stores such as supermarkets employ fluorescent lighting inside or outside of refrigerated storage units. In this context, the artificial light intensity in dairy display units may, for example, range from 20 and 500 footcandles. However, to provide reliable protection in "bright light" display units, preferred packaging materials should allow the filled dairy product to retain acceptable flavor after exposure to 200 footcandles illumination at a temperature of 38° F. for 14 days. With regard to light-excluding, i.e., "opaque", containers, these include, for example, both paperboard cartons and plastic or glass bottles. The walls of the containers exclude at least 90% (Optical Density of at least 1.0, and preferably 98% (Optical Density of at least 1.7) of the incident visible light as described above. Opaque paperboard cartons which are generally coated with a thin layer of polyethylene, and which hold either one or two quarts liquid were obtained from the International Paper Company. Opaque white polyethylene bottles capable of holding from one pint to one gallon were obtained from Shelburne Plastics, Inc.

The term "off-flavors" in the context of a dairy product refers to any new taste or smell, often volatile and unpleasant which may appear following initial packaging. Some common off-flavors include rancid or oxidized fat flavor, acid or sour flavor, musty or earthy flavor, sulfurous flavor, acetone-like flavor and tallowy flavor.

A "flavoring agent", defined in the same context, is an edible substance which, when added to a dairy product, beneficially alters the taste or smell of the product (see Kahn et al., U.S. Pat. No. 5,063,074 for a detailed definition). The flavoring agent may be used to correct or mask an off-flavor, e.g., chocolate or banana flavor. Alternatively, the flavoring agent may replace or reinforce a natural dairy flavor such as a mikfat-associated flavor which is lacking in skim milk-derived products. Thus, in a filled dairy product which lacks milkfat but contains a non-tropical vegetable oil (e.g., Kahn et al., U.S. Pat. No. 5,063,074), a premix is added, which combines natural milk distillate as a flavoring agent. In fact, it is the experience of Applicants that a tasteless and odorless vegetable oil, such as that described by Kahn et al., contributes an unpleasant oily mouthfeel and aftertaste to a filled dairy product, which otherwise lacks milkfat. Such a deficiency in flavor and mouthfeel is evident in a filled milk containing soybean oil and lacking milkfat (and furthermore, lacking any flavoring agent; see Example 6 below, Group A results). This deficiency only becomes more significant with aging of the filled dairy product as oxidized flavors become more obvious.

Filled dairy products described in the present invention may contain unmodified milkfat, i.e., regular milkfat, or alternatively, milkfat which has been separately treated to remove or extract cholesterol, e.g., by a non-hydrogenation procedure such as described by Marschner et al. in U.S. Pat. Nos. 4,804,555 and 4,996,072 and other equivalent methods known in the art, for example, employing supercritical fluid extraction, or extraction using cyclodextrans. Such treated milkfats are termed herein cholesterol-reduced.

With regard to the relative fat content of a particular type of dairy product, the term "full fat" refers to the standard food identity fat content, e.g., milk, approximately 3.25% fat by weight, and butter, approximately 80% fat by weight. The term "reduced fat" content refers to a decrease of at least 25% below the regular or "full fat" content of the food product. The term "low fat" content refers to a food product containing no more than 3 g of fat per serving. For milk having a serving size of 244 g, the 3 g fat limit defines low fat milk as containing no more than 1.23% by weight fat.

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Other features and advantages of the invention will be apparent from the following description of the preferred embodiments thereof, and from the claims.

DETAILED DESCRIPTION OF THE PREFERRED EMBODIMENTS

The drawing will first briefly be described.

DRAWING

FIG. 1 is a diagrammatic representation of lipoprotein metabolism.

FATTY ACID BALANCE

To understand the significance of, and reason for balancing the proportion of saturated and polyunsaturated fatty acids by selecting or engineering a single vegetable oil species, or by blending two or more vegetable oils and/or fats for including in the fat-containing foods mentioned above such as cooking fats, prepared baked foods, dietary foods, and the like, one must understand some of the important parameters governing lipoprotein and cholesterol synthesis and catabolism (see FIGURE).

The LDL/HDL ratio, and changes in this ratio depend upon a number of metabolic variables such as hormonal, metabolic, environmental and nutritional perturbations including changing dietary fat compositions which affect lipoprotein levels. As detailed in FIG. 1, it can be seen that both LDL and HDL are derived, in part, by the catabolic events resulting in the breakdown of VLDL (very low density lipoprotein), the TG (triglyceride)-rich lipoprotein secreted by the liver for the purpose of delivering TG to muscle for energy generation or to adipose tissue for storage. In humans, the breakdown of VLDL is a major source of HDL as well as the primary origin of LDL as described by Grundy et al., 31 J. Lipid Res. 1149, 1990. Thus, the potential mass for both HDL and LDL generation is dependent, in part, upon the production rate (mass per unit time) of VLDL secreted by the liver. On the other hand, reduction in the final pool of circulating LDL depends both upon the proportion of the VLDL remnants which are retained and cleared by the liver directly (reducing diversion to LDL) as well as the rate of LDL removal by the liver once LDL is formed. Both VLDL remnants and LDL are cleared via liver receptors (LDL.sub.r), and both represent a "sink" for receiving HDL cholesterol esters (CE) via CETP (cholesterol ester transfer protein, see below), thereby reducing the HDL pool once it has been formed. The main function of HDL in this cholesterol-shuttle pathway is to "clean-up" the cholesterol excess "spilled" during VLDL catabolism and then deliver it (as indicated above) as CE either to VLDL remnants or to LDL. These lipoproteins can then carry cholesterol back to the liver for excretion as bile acids (or biliary free cholesterol). Both the catabolism of VLDL involving release of TG, and the CE shuttle from HDL to VLDL-LDL are controlled by proteins that are affected by dietary fat. The former process is modulated by lipoprotein lipase (LPL) and the latter by the transfer protein CETP. These proteins are affected oppositely by the presence of saturated (SAT) and trans (elaidic acid-containing) fats on the one hand, versus polyunsaturated (POLY) fat on the other hand. SAT and trans fats induce increased CETP activity which is associated with increased LDL, and trans fats can even decrease HDL. However POLYs reduce the activity of CETP and enhance LPL activity and favor formation of HDL from VLDL as shown by Demacker et al., 21 Eur. J. of Clin. Invest. 197, 1991.

Applicant and other investigators have found that dietary fatty acids consumed in the form of natural fats or fat blends affect different lipoproteins and their concentrations in a number of ways. For example, for more than 30 years it has been appreciated that saturated fat increases total cholesterol (TC), whereas polyunsaturates decrease it, and monounsaturates were thought to be neutral (see Hegsted et al., 17 Am. J. of Clin. Nutr. 281, 1965, Hegsted et al., 57 Am. J. of Clin. Nutr. 875, 1993, and Heyden, 38 Ann. Nutr. Metab. 117, 1994). More recently, investigators have focused on nutritional variables by which the different species of lipoproteins, as opposed to TC, are affected. The consensus is that most saturated fatty acids consumed as fats, i.e., twelve to fourteen carbon saturated fatty acids including lauric, myristic, and palmitic acids (12:0, 14:0, and 16:0 respectively), have the potential for elevating both LDL and HDL, although the relative increase in LDL tends to be greater than that for HDL (see Grundy et al., 31 J. Lipid Res. 1149, 1990, Pronczuk et al., 8 FASEB J., 1191, 1994, Katan et al., 60 suppl. Am. J. Clin. Nutr. 1017S, 1994 and Mensink et al., 12 Arteriosclerosis and Thrombosis 911, 1992). Adding to the complexity, 14:0-rich TGs are more cholesterolemic than 16:0-rich TGs (see Hegsted et al., 17 Am. J. Clin. Nutr. 281, 1965, Sundram et al., 59 Am. J. Clin. Nutr. 841 1994, Hayes et al., 53 Am. J. Clin. Nutr. 491, 1991, and Hayes et al., 6 FASEB J. 2600, 1992), and the impact of 16:0 is highly dependent on the host "metabolic setpoint" for TC in the serum at the time of intervention. Thus in people with high TC, 16:0 acts as a cholesterol-raising fatty acid, but at TC<200 mg/dl 16:0 typically appears neutral, neither raising nor lowering TC (see Heyden, 38 Ann. Nutr. Metab. 117, 1994, and Hayes et al., 53 Am. J. Clin. Nutr. 491, 1991). On the other hand, 14:0-rich TGs are always cholesterol-raising, suggesting a different regulatory role for 14:0 and 16:0. Natural TGs, i.e. fats containing the 12:0 fatty acid also contain 14:0, so for all practical purposes they can be considered together (12:0+14:0) and separate from 16:0, which is generally the most prevalent saturated fatty acid in fats derived from plant and animal sources, often without any 12:0+14:0. Surprisingly, stearic acid (18:0) seems to be neutral in its regulatory behavior over TC (see Hegsted et al., 57 Am. J. Clin. Nutr. 875, 1993 and Katan et al., 60 suppl. Am. J. Clin. Nutr. 1017S, 1994).

Only one fatty acid, linoleic acid (18:2n6 or 18:2), is generally acknowledged to be cholesterol-lowering. As an essential or required dietary polyunsaturated fatty acid, it alone among all of the POLYs (including linolenic or 18:3n3, eicosapentenoic (EPA) or 20:5n3, and docosahexenoic acid (DHA) or 22:6n3) consistently lowers TC, especially lowering LDL-C but also decreasing HDL-C at high dietary intake of POLYs (Grundy et al., 31 J. Lipid Res. 1149, 1990, Hegsted et al., 17 Am. J. Clin. Nutr. 281, 1965, and Hegsted et al., 57 Am. J. Clin. Nutr. 875, 1993). In fact, this tendency for 18:2 to lower HDL has even led to warnings against recommending POLYs as a means for lowering TC. Rather, the recommendation has been offered that monounsaturated fats (MONOs) containing oleic acid (18:1) should replace saturated fat as much as possible because MONOs do not lower HDL like POLYs do, and replacing saturates with MONOs will primarily lower LDL as suggested by Grundy et al., 31 J. Lipid Res. 1149, 1990.

As applicant will describe below, the later statement is true, but it ignores the critical role of POLYs, and the fact that it is a critical balance between dietary intake of SATs and POLYs (both at moderate intake) which actually allows HDL to increase to yield the highest serum HDL/LDL ratio, at least in humans with normal cholesterol metabolism.

Over the past few years a number of nutritional experiments using animal models and humans are relevant to Applicant's finding of fatty acid proportions required for generating the highest HDL/LDL ratio. The first relevant study was in monkeys (Hayes et al., 53 Am. J. Clin. Nutr. 491, 1991). In that report it was found that for SATs, 16:0 increased TC less than 12:0+14:0, but quite surprisingly 16:0 had an effect on TC very similar to POLYs (18:2) when 5% of the daily dietary calorie intake (abbreviated 5% en) was exchanged between these 2 fatty acids (between 5–10% en as 18:2, i.e. Diets 4 vs. 5 in the cited study). At the time of the study, the authors failed to appreciate the significance of the fact that once 5% en as 18:2 in the daily diet has been achieved, additional dietary 18:2 does not really exert much effect on TC and can be exchanged for other "neutral" fatty acids without altering TC appreciably. This relationship has been described as the "threshold effect" for 18:2 (Hayes et al., 6 FASEB J. 2600, 1992 and Pronczuk et al., 8 FASEB J. 1191, 1994).

In a second study in rhesus monkeys (Khosla et al., 1083 Biochem. et Biophys. Acta 46, 1991), the authors explored possible metabolic reasons for differences observed in TC during the exchange of (16:0+18:1) for (12:0+14:0) (Diet 4 versus Diet 2 in the cited study). It was found that the former fatty acids (16:0+18:1) led to 3-fold more VLDL output than the (12:0+14:0) diet, and that the (12:0+14:0) diet produced a larger LDL pool and a poorer (lower) HDL/LDL ratio. The authors interpreted this to mean that dietary (12:0+14:0) fatty acids were worse than 16:0 (and 18:1) in terms of raising LDL, presumably because (12:0+14:0) down-regulate the $LDL_r$ making it difficult for VLDL remnants and LDL particles to be cleared by the liver. This ultimately causes LDL to accumulate.

In a third monkey study (Khosla et al., 55 Am. J. Clin. Nutr. 51, 1992) the effect of high dietary intake of SAT 16:0 in the form of palm oil, versus high dietary intake of MONO 18:1 in the form of high oleic safflower oil, and also versus high dietary intake of POLY 18:2 in the form of high linoleic safflower oil was examined. Here the TC response was animal species specific, with all three fats causing an equal TC response in rhesus. However the high dietary 18:2 (at 30% en) produced lower TC in the cebus species by virtue of an undesirable depressed HDL-C level while the LDL-C was unaffected by all three diets in both species. These data indicated that genetic differences can affect the sensitivity to 18:2 in the diet, but that 16:0, 18:1, and 18:2 can appear to exert similar effects when lipoprotein metabolism is unimpaired and when essentially no dietary cholesterol is present to interfere with LP metabolism (especially by decreasing LDL receptor number and LDL clearance rate).

An interesting observation and measurement recorded in the above cited study and unexplained until now was a favorable HDL/LDL ratio which was greater in monkeys fed the 16:0-containing SAT diet than the MONO or POLY diet. This observation contradicted the generally held belief that dietary SATs should be avoided in favor of POLYs and MONOs. However, this early measurement taken together with the more extensive new data provided in Appendix I now indicate that saturated fatty acids are a necessary dietary component for increasing HDL and increasing the HDL/LDL ratio in the serum.

In other previous experiments using saturated animal fats blended with POLYs described in Perlman and Hayes, supra, it is noted that rodents (gerbils and hamsters) and monkeys (cebus) exhibited unexpectedly increased HDL/LDL lipoprotein ratios when corn oil (rich in 18:2) was blended into animal fats stripped of cholesterol. These data are also consistent with the model now proposed in which a balanced ratio of SATs and POLYs in the diet may be the most important consideration in modulating lipoproteins to increase HDL and maximize the HDL/LDL ratio.

The discovery confirming and validating applicant's new model appears in the human nutritional study involving three different diets described in Sundram et al. (hereby incorporated by reference in totality, Nutrional Biochemistry Vol 6:179–187, 1995). The most critical results from this study are summarized in Table III.

TABLE III

HDL CONCENTRATION IN HUMAN SERUM VARIES WITH RATIO
OF SATURATED TO POLYUNSATURATED FATTY ACIDS IN DIETARY FAT

| Dietary Fat | Dietary Fat Composition (Weight Percentage) | | | Percent Dietary Energy (Percentate of Daily Calories) | | | Serum Cholesterol (mg/dl concentration) | | |
|---|---|---|---|---|---|---|---|---|---|
| (Code) | SAT | MONO | POLY | 16:0 SAT | 18:1 MONO | 18:2 POLY | HDL-C | LDL-C | TC |
| CAN | 7 | 57 | 36 | 4 | 17 | 6 | 49 | 97 | 177 |
| POL | 44 | 45 | 11 | 11 | 13 | 3.5 | 49 | 102 | 181 |
| AJA | 30 | 37 | 33 | 8 | 12 | 7 | 57 | 96 | 179 |

These diets included one containing low dietary SATs combined with moderate POLYs and high MONOs (canola oil diet-abbreviated CAN), a second containing high dietary SATs combined with low POLYs and moderate MONOs (palm olein-abbreviated POL), and a third containing moderate dietary SATs combined with moderate POLYs and moderate MONOs (soybean oil-palm olein-canola oil blend-abbreviated AHA). Indeed, all three fat-containing diets produced equal TC and similar LDL-C, but the AHA fat blend increased HDL-C by 20% (see Table III) relative to the other two diets. Thus, Applicant unexpectedly discovered that normolipemic people (i.e., people with normal lipoprotein metabolism and exhibiting serum TC values of <200 mg/dl) appear to require moderate levels of both SATs and POLYs which, in appropriate total dietary amounts, produce an increased HDL concentration and increased HDL/LDL ratio in the serum.

In order to provide a general method for maximizing the HDL/LDL ratio in human serum it is useful to understand the physiological basis by which the HDL/LDL ratio may be altered. Returning to FIG. 1 and the experimental observations reported on herein, it appears that SATS (16:0 in the above diet) drive VLDL output, maximizing the potential for HDL production (i.e., increasing the HDL precursor pool of VLDL). Since high dietary levels of MONOs did not increase HDL while moderate levels of SATs did increase HDL, it would appear that 16:0 (not 18:1) may have been responsible for the greatest VLDL output in the previous rhesus study (Khosla et al., 55 Am. J. Clin. Nutr. 51, 1992). Secondly, it seems that an adequate intake of POLYs > which must exceed the 3.3% en shown to be sub-optimal in the low-POLY diet in the appendix is needed to assure up-regulated or stimulated $LDL_r$ activity. This level of POLYs is estimated to be at least 5–6% en and has been described elsewhere as "assuring the 18:2 threshold requirement" (Hayes et al., 6 FASEB J. 2600, 1992 and Pronczuk et al., 8 FASEB J. 1191, 1994). This intake of POLYs also assures that VLDL catabolism and LDL clearance proceeds efficiently and rapidly (decreasing plasma LDL) while sparing the need for HDL "clean-up" (ultimately increasing available HDL). Viewed as a balancing process, adequate SATs are needed to enhance HDL precursor output (as VLDL) and adequate POLYs are needed to keep LDLr up-regulated to enhance LDL and VLDL remnant clearance by the liver. Together this combination results in the highest HDL and lowest LDL levels in the serum. To applicant's knowledge neither this combination of fatty acids nor this rationale for metabolic function has ever been recognized, let alone demonstrated in humans prior to this time.

The importance of diversifying the dietary intake of polyunsaturated fatty acids to include one or more of the omega3 polyunsaturates (i.e., .alpha.-linolenic acid (18:3, omega3), eicosapentenoic acid (EPA) and docosahexenoic acid (DHA), in addition to linoleic acid (18:2, w6), has recently been pointed out by Charnock et al. (3.sup.rd Int. Symp. on Lipid Metabolism in the Normal and Ischemic Heart, September 1991) and by McLennan et al. (19 Aust. N Z J. Med. 1, 1989). According to these investigators, adding the above-mentioned omega3 polyunsaturated fatty acids to the diet improved the mechanical performance and the electrical stability of the marmoset heart. In this animal model the incidence of ventricular fibrillation was reduced while ventricular ejection, peak filling rate and end diastolic volume increased when compared to animals fed similar diets containing only polyunsaturates of the w6 type, e.g., linoleic acid. In marmosets fed saturated animal fats in place of comparable amounts of sunflower oil (linoleic acid-rich oil) or fish oil (omega3-rich oil), cardiac performance deteriorated significantly with respect to both mechanical and electrical parameters.

As taught in the present invention, there are several straightforward means of providing a mix, and controlling the balance of saturated and polyunsaturated fatty acids in ones daily dietary fat. In the extreme case, the strictly controlled use of liquid and/or solid dietary formulations which provide all of the dietary fat can be used to insure this balance. In a moderately controlled setting, institutional preparation of food for resident populations allows the monitored use of fats, e.g., hospital, university, and military kitchens, in which appropriately balanced fat blends can be used throughout the food preparation scheme. In addition, manufacturers of prepared food such as commercial bakers can use appropriately balanced blends of fats and oils.

EXAMPLE 1

Fat Blends for Increasing the HDL Concentration and the HDL/LDL Ratio

Two parts palm oil (44% palmitic acid, 9% linoleic acid) are blended with one part corn oil (11% palmitic acid, 58% linoleic acid) to provide a balanced fat blend containing approximately 33% palmitic acid (16:0) and 25% linoleic acid (18:2). When consumed as the principal and essentially the sole source of dietary fat in the daily diet, and representing approximately 30% of the dietary energy this fat blend will increase the level of HDL cholesterol in human serum and the HDL/LDL ratio compared to a similar diet in which the proportion of either palmitic acid or linoleic acid is 3-fold lower.

EXAMPLE 2

Other Fat Blends for Increasing HDL and the HDL/LDL Ratio

One part palm oil (44% palmitic acid, 9% linoleic acid) is blended with one part cottonseed oil (23% palmitic acid, 52% linoleic acid) to provide a fat blend containing approximately 34% palmitic acid and 31% linoleic acid. One part palm oil is blended % with one part soybean oil (10% palmitic acid, 51% linoleic acid and 7% linolenic acid) to provide a fat blend containing approximately 27% palmitic acid, 30% linoleic acid and 3% linolenic acid. Alternatively, one part coconut oil (approximately 70% lauric, myristic, and palmitic acids, and 2% linoleic acid) is blended with one part sunflower oil (6% palmitic acid, 66% linoleic acid) to provide a different balanced fat blend containing approximately 38% C12–C16 mixed saturated fatty acids and 34% linoleic acid. Alternatively, in a three component system, one part palm kernel oil (47% lauric acid, 16% myristic acid, 8% palmitic acid, and 2% linoleic acid) is blended with one part corn oil (11% palmitic acid and 58% linoleic acid) and one part canola oil (4% palmitic, 20% linoleic acid and 9% linolenic acid) to provide a fat blend containing 29% C12–C16 mixed saturated fatty acids, 27% linoleic acid, and 3% linolenic acid. In another three component system termed the AHA blend (see Table I), four parts palm oil are blended with five parts soybean oil and one part canola oil to provide a fat blend containing 26% palmitic acid, 29% linoleic acid, and 3% linolenic acid. In still another three component system, three parts palm olein (39% palmitic acid, 11% linoleic acid) are blended with one part cottonseed oil (23% palmitic acid, 52% linoleic acid) and one part safflower oil (6% palmitic acid, 74% linoleic acid) to provide a fat blend containing 29% palmitic acid and 32% linoleic acid.

EXAMPLE 3

Oxidation-Resistant Fat Blends for Food Preparation as Well as for Increasing the HDL Concentration and the HDL/LDL Ratio Consistent with Examples 1 and 2, blends useful for increasing the HDL level and the HDL/LDL ratio in human serum include four to nine parts palm olein (39% palmitic acid, 11% linoleic acid) blended with one part of corn oil (11% palmitic acid, 58% linoleic acid) to provide a dietary fat blend containing approximately 33% to 36% palmitic acid and 20% to 16% linoleic acid. Similarly, two parts palm olein are blended with one part of corn oil to provide a fat blend containing approximately 30% palmitic acid and 27% linoleic acid. Likewise, as illustrated in Example 1, two parts palm oil are blended with one part corn oil for use as a dietary fat. These and other blends of vegetable fats and oils have been found to be valuable as ingredients in baked, fried, and other prepared foods, e.g., salad dressings, desserts, etc. because of the increased oxidative stabilities of these blends in combination with their metabolic benefits already described. The increase in oxidative stability for the polyunsaturated vegetable oil component in these blends is reflected in a longer shelf life for foods prepared using these blends, and a longer cooking (i.e., frying) lifetime for these blends when they are maintained at an elevated temperature (approximately 350.degree. F.) for many hours.

By way of specific example, when blended with palm oil or palm olein, the oxidation-resistance of certain polyunsaturated vegetable oils is increased relative to that of the same oil when heated separately from the blended composition. In this Example and in Table IV, the stability of various oils and blends was measured by the Rancimat method in which the oxidative stability is directly proportional to the Rancimat number provided. A fat blend in which the oxidative stability of the blend is at least 25% greater than that of the polyunsaturated vegetable oil component in the blend is considered an oxidation-resistant blend for the purposes of this invention.

The extent of oxidation-resistance in such blends has been found to vary widely depending upon the type of vegetable oil (e.g., corn versus soybean oil) and the extent of its dilution into the saturated fat such as palm fat. Accordingly, it is apparent from Table IV that at higher dilutions of polyunsaturated vegetable oils (e.g., 5-fold and 10-fold dilutions of soybean oil into the palm fats), the fat blends maintains good stability. However, when diluted only 3.3-fold (see 2.3:1 column in Table IV), and within the composition range nutritionally useful in the present invention, the oxidative stability of the soybean oil-palm fat blends can fall to approximately the same level as the unblended vegetable oil (cf. 7.6 and 5.6 for the blends versus 6.3 for the soybean oil alone). Surprisingly however, Table IV reveals that corn oil can be stabilized against oxidation at both lower (3.3-fold) and higher (5 and 10-fold) dilutions with palm fat. Thus, the oxidative stability of the corn oil-palm blends is at least two-fold greater than the corn oil alone (cf. 11.2 and 9.9 for the lower dilution blends versus 4.8 for the corn oil alone). The results from this Table and from previous unpublished experiments of Applicant have shown that the oxidative stability of fat and oil blends is unpredictable and can only be determined by experimentation. It is significant that the proportions of a number of fats and oils in such blends which are useful in the diet for controlling cholesterol levels as taught herein, are also useful owing to their oxidative stabilities.

TABLE IV

OXIDATIVE STABILITY OF FAT
(Rancimat method*)

|  | Ratio | Palm olein:Polyunsaturated oil |  |
| --- | --- | --- | --- |
| Polyunsaturated oil | 9.1 | 4.1 | 2.3:1 |
| Soybean | 16 | 14.4 | 7.6 |
| Corn | 16.7 | 13.5 | 11.2 |
|  | Ratio | (Palm oil:Polyunsaturated oil |  |
| Polyunsaturated oil | 9:1 | 4:1 | 2.3:1 |
| Soybean | 14.4 | 10.2 | 5.6 |
| Corn | 15.3 | 12.2 | 9.9 |

OXIDATIVE STABILITY OF PURE FATS AND OILS

| Palm olein | 20 |
| --- | --- |
| Palm oil | 21.2 |
| Soybean oil | 6.3 |
| Corn oil | 4.8 |

*The Rancimat method determines the oxidative and thermal stability towards oxidative decomposition in oils and fats. The oil sample is exposed to a stream of atmospheric oxygen at elevated temperatures giving rise to organic acids in the oil/fat. These volatile products are trapped in a measuring vessel filled with distilled water and continuously detected with a conductivity cell. The measurements are then evaluated by a control unit which records the induction time of the sample. The progress of the oxidation curve determined in this manner virtually parallels the development of the peroxide values in the oils being tested As described above, the present invention also provides filled dairy products with desirable fatty acid content and taste characteristics, and provides a method for maintaining flavor stability.

With respect to taste, although Kahn et al., supra, asserts that a vegetable oil is chosen which is "tasteless and odorless", it has been found, through Applicant's experimentation, that flavoring agents are needed to compensate for, and/or mask the oily mouthfeel and flavors present in a filled milk whose fat portion is exclusively non-tropical vegetable oil such as soybean, safflower, corn, cottonseed, sunflower, peanut, olive, and canola oils.

In addition, the flavor stability of filled milk containing polyunsaturated fats is severely limited by exposure of the milk to visible light. Light exposure is a problem because fluorescent lighting used in refrigerated dairy cases tends to be bright, with typical illumination intensities ranging between approximately 50 and 250 footcandles at the surface of the dairy product. Both Arcadipane, supra, and Strong et al., supra, recognize that off-flavors could develop rapidly in a polyunsaturated fat-filled milk. They opted to use either partially hydrogenated or monounsaturated fat, but did not recognize that flavor stability could be maintained in a polyunsaturated fat-filled milk if visible light were excluded.

In the present invention, it has been demonstrated that the flavor quality of a filled milk containing equal amounts of a polyunsaturated vegetable oil, e.g., soybean oil, and milkfat is degraded-at an unexpectedly rapid rate by exposure to visible light over a very broad wavelength range. That is, after only 4 to 8 hours of exposure to fluorescent lighting, a substantial level of oxidized flavor was reported (see Example 5 below). By comparison, over a similar exposure interval, regular milk (containing only milkfat) has been shown to undergo very little flavor change. Applicants have clearly demonstrated that an adequate shelf life, e.g., 14 days, and retention of natural milk flavor in a filled milk product containing polyunsaturated vegetable oil(s) is provided by dark storage or, alternatively, packaging in containers which exclude most (preferably greater than 90%) or all of the visible light. Applicant is aware of no relevant literature describing the photo-decomposition of filled milks. Indeed, the generally accepted methods for preventing or at least minimizing the development of rancidity in polyunsaturated vegetable oil-containing food products have been to:

(i) partially hydrogenate the oil as in Arcadipane, supra, or utilize a monounsaturated oil such as canola oil which is less susceptible to oxidation than soybean oil, for example.

(ii) add a fat-soluble and/or water-soluble antioxidant such vitamin E and/or vitamin C into the milk (iii) package the food under nitrogen gas in packaging materials which excludes oxygen.

(iv) dilute the polyunsaturated vegetable oil with between one and ten parts of saturated animal fat (such as milkfat). Perlman et al., U.S. Pat. No. 5,382,442, has previously shown that such dilution could substantially increase the resistance to rancidity (oxidation-resistance) of the oil.

Surprisingly, as shown in tests below with a filled milk containing 0.5% milkfat and 0.5% soybean oil, neither vitamin E-acetate (200 International Units (IU) tocopherol acetate per quart) in the fat portion of the milk, nor vitamin C (100 mg ascorbic acid per quart) in the aqueous portion of the same milk increased the resistance of the milk to photo-induced flavor degradation. Furthermore, the 1:1 dilution of vegetable oil with milkfat in the filled milk (strategy (iv) above) did not provide any apparent flavor stability.

Applicants have discovered that a major contributor to the development of off-flavors in the combined polyunsaturated vegetable oil and milkfat-containing dairy products in the present invention is not aging or simple oxidation from contact with air, but exposure of these dairy products to visible light (presumably in the presence of dissolved oxygen). Thus, according to the present invention, natural milk flavor can be preserved in a filled dairy product containing a high proportion of polyunsaturated fatty acids (i.e., 15%–40% by weight of the total fat), by reducing or preventing exposure to all wavelengths of visible light (e.g., by storing the product in a substantially light-opaque container). The container preferably excludes greater than 90% of visible light between the wavelengths of 300 nm and 700 nm. Without such storage protection, off-flavors develop rapidly as a result of photochemical reactions in a dairy product exposed to visible light such as artificial fluorescent lighting in a refrigerated dairy storage case.

Unlike vitamins A and $B_2$ in milk, which are selectively degraded by exposure to visible light below a wavelength of 455 nm, Applicants have discovered that light across the entire visible spectrum can cause off-flavor development in polyunsaturated fat-containing milk. For example, a semi-opaque jug (blocking about 90% of the incident light between 380 nm and 500 nm), and known to substantially protect vitamins A and $B_2$ against photodecomposition under 200 foot candle fluorescent light illumination, failed to protect the flavor of 1% milk in which the fat was a 50–50 blend of soybean oil and milkfat (see Example 5 below).

Flavor stability was also examined when this same milk was stored in colored cellophane-wrapped translucent milk jugs. When the milk was packaged in a blue cellophane-wrapped translucent jug (which selectively transmits light between 400 nm and 540 nm), it was found to be less susceptible to flavor degradation than the same milk packaged in a yellow cellophane-wrapped translucent jug (transmitting light between 300 nm and 400 nm, and above 500 nm).

Furthermore, both green cellophane wrapping (essentially yellow plus blue color, selectively transmitting light only between 490 nm and 570 nm), as well as red cellophane wrapping (transmitting light only above a wavelength of 590 nm) permitted rapid development of off-flavors in the polyunsaturated fat-containing milk (see Example 5). Therefore, the active spectrum for off-flavor development is very broad, and differs markedly from the limited range of wavelengths of light (below 455 nm) which cause vitamin A and $B_2$ degradation.

Filled dairy products of the present invention are typically based upon skim milk (and/or a reduced milkfat-containing milk or regular milk), homogenized with a premix which comprises heavy cream (or other concentrated source of milkfat), plus at least one polyunsaturated vegetable oil (preferably containing both linoleic acid and linolenic acid, such as freshly refined and deodorized soybean oil), plus an effective concentration of at least one emulsifier (such as a mono- and diglyceride capable of maintaining said combination of polyunsaturated and saturated fats as a stable emulsion in the filled dairy product).

For many years, it has been known that an increased proportion of saturated fats in ones diet tends to increase both LDL "bad" cholesterol as well as HDL "good" cholesterol. On the other hand, increasing the proportion of polyunsaturated fats in ones diet tends to decrease both LDL and HDL cholesterol. Recent human clinical studies described by Sundram et al. in U.S. Pat. No. 5,578,334 and Sundram et al., U.S. Pat. No. 5,843,497 has shown that an approximately equal balance of dietary polyunsaturated and saturated fatty acids present in vegetable fats generally provides the best serum cholesterol profile in terms of reducing the LDL cholesterol level while sustaining or increasing HDL cholesterol to produce a favorable increase in the ratio of HDL to LDL cholesterol. According to the studies of Sundram et al., supra, the desirable composition of dietary fats when averaged overall should be: between 15% and 40% by weight polyunsaturated fatty acids and between 20% and 40% saturated fatty acids. Furthermore, to achieve the maximum benefit from this balanced intake of polyunsaturated and saturated fatty acids, certain cholesterolemic components in the diet should be limited. In particular, the unnatural trans fats such as elaidic acid produced by partial hydrogenation of polyunsaturated vegetable oils should be limited in the diet. In fact, simple extrapolation of data from a recently published major clinical study (Hu et al., N. Eng. J. Med. 1997; 337:1491–1499) shows that for each 1% increase in fat intake, trans fats increase the risk of coronary heart disease approximately 46% versus only 3% for an equivalent amount of saturated fat. Therefore, for health-conscious individuals, the idea of incorporating a partially hydrogenated trans-rich vegetable oil, and reducing polyunsaturated fatty acid content to between 2% and 8% linoleic acid in a food such as milk, according to Arcadipane (U.S. Pat. No. 5,393,551), would be unacceptable. Dietary consumption of cholesterol should also be controlled, e.g., by increasing consumption of low fat dairy products, and reducing the consumption of fatty meat products which are high in cholesterol. Even the monounsaturated fat-filled dairy products of Strong et al., supra, containing no more than 12% by weight of polyunsaturated linoleic acid provide less than the currently recommended proportion of polyunsaturated fatty acids in a balanced fat diet.

Consistent with the objectives of Sundram et al. in U.S. Pat. No. 5,578,334 and Sundram et al., U.S. Pat. No. 5,843,497 (which limits and balances saturated fats with polyunsaturated fats in food, while simultaneously controlling the overall level of fat and cholesterol in foods), Applicants have produced filled milk (and other dairy products such as filled ice cream), in which approximately one-third to two-thirds of the milkfat in a dairy product is replaced by a polyunsaturated vegetable oil. When approximately 50% of the milkfat is replaced by natural soybean oil, for example, the cholesterol and saturated fat contents of the dairy product are decreased by nearly half, while the proportion of polyunsaturated fat in the product is beneficially increased nearly 10-fold (see Table I).

Despite the health benefits obtained by consuming an increased proportion of polyunsaturated fat in the diet, the commercial food industry has favored the use of either a partially hydrogenated oil (Arcadipane, U.S. Pat. No. 5,393,551) or a monounsaturated-rich vegetable oil (Strong et al., U.S. Pat. No. 5,580,600) as the fat constituent in a filled dairy product such as milk. The poor oxidative stability of polyunsaturated fats in filled dairy products, and the problem of rapidly developing off-flavors in such products has discouraged new product development in this area. When polyunsaturated vegetable oil has been included in the fat constituent of filled dairy products, some compensating measure to deal with the oxidation problem is usually evident. For example, in Kahn et al., U.S. Pat. No. 5,063,074, one or more flavoring agents are added to these polyunsaturated fat-containing products. These flavoring agents serve, in part, to mask off-flavors which develop as the products are shipped through distribution, and then stored prior to consumption. The use of vitamin E, an antioxidant, in a number of different filled dairy products including milk, has been noted in the literature. Whether or not this vitamin or, for example, vitamin C (a water-soluble antioxidant) is effective in extending the shelf-life and preserving the flavor in these products is unclear. Indeed, it appears that, until now, the knowledge has been lacking that the primary cause of flavor degradation and limited shelf-life in polyunsaturated fat-filled dairy products is exposure of these products to visible light.

It has been appreciated that visible light can degrade a variety of vitamins in milk with varying speed, including vitamin A (retinol) and its provitamin, beta-carotene, vitamins $B_2$ (riboflavin), and vitamin C (ascorbic acid). The photodegradation of riboflavin in milk has been examined in detail, and is induced by visible light between the wavelengths of 415 nm and 455 nm. The rapidity of its degradation (and that of other vitamins) depends upon the intensity, duration and wavelength of light, the product storage temperature, and light transmittance through the product and its packaging. Skim milk, for example, is more transparent than regular milk (which contains emulsified fat), and its vitamins are therefore more susceptible to photodegradation.

To avoid any need for flavorings to compensate or mask any unpleasant or oxidized flavors in polyunsaturated vegetable oil-filled dairy products, research was conducted into sources and processes of oily flavor and off-flavor development. As a result of this research, filled milk and other filled dairy products containing polyunsaturated vegetable oil have been successfully produced without addition of corrective flavorings. In fact, the taste and mouthfeel of a non-hydrogenated soybean oil-filled milk, for example, can approximate either whole milk, or a reduced fat-containing milk, e.g., 2% and 1% fat-containing milks. Furthermore, the shelf-life of various filled dairy products can be comparable to that of the corresponding 100% milkfat-containing products. However, the processing and handling of a refined and deodorized vegetable oil is critical for obtaining such high quality products. That is, following the vacuum distillation process used in refining and deodorizing a vegetable oil such as soybean oil, the oil is sparged, i.e., bubbled, with nitrogen to displace residual oxygen, and then stored and shipped under a blanket of nitrogen gas. Thus, nitrogen is introduced during loading the oil into a tank truck, for example, used in transporting the oil. This has proven to be important for avoiding the later development of off-flavors in filled dairy products, particularly when the vegetable oil triglycerides being utilized not only contain a substantial proportion of esterified linoleic acid, but also a significant amount of the triply unsaturated esterified linolenic acid which is very susceptible to oxidation. Such is the case with non-hydrogenated soybean oil containing approximately 50–55% esterified linoleic acid and 7–8% esterified linolenic acid. Accordingly, for the purposes of the present invention, it is desirable to obtain freshly refined and deodorized vegetable oil, e.g., soybean oil, which has been sparged with nitrogen, and then shipped rapidly to the dairy product manufacturer, preferably under a blanket of nitrogen.

The following method and examples are given to further illustrate the present invention. The scope of the invention is not, however, meant to be limited to the specific details of the examples.

METHOD

Finding an Appropriate Ratio of Milkfat (Butter) and Vegetable Oil to Provide Balanced Fatty Acid Nutritional Profile for Improving HDL/LDL Serum Cholesterol Ratio Purpose: As described above, recent human clinical studies (see Sundram et al. in U.S. Pat. No. 5,578,334 and Sundram et al., U.S. Pat. No. 5,843,497) have shown that an approximately equal balance of dietary polyunsaturated and saturated fatty acids provided in vegetable fat blends generally provide the best serum cholesterol profile in terms of reducing the LDL cholesterol level while sustaining or increasing HDL cholesterol to produce a favorable increase in the ratio of HDL to LDL cholesterol. Applicants have obtained similar results in animal nutritional studies using blends of saturated animal fat (e.g., milkfat) and polyunsaturated vegetable oil (e.g., soybean or corn oil). In U.S. Pat. No. 5,578,334, it is shown that the beneficial range for the linoleic acid content of a fat blend is between approximately 15% and 40% by weight, while the beneficial range for saturated fatty acids including palmitic acid, myristic acid, lauric acid, stearic acid, and combinations thereof is between 20% and 40%. Accordingly, the following table (Table V) is provided as an illustration to show how appropriate blend ratios of milkfat and polyunsaturated vegetable oil can be selected for use in filled dairy products. A nearly optimal balanced fatty acid ratio, (i.e., a 1:1 ratio of polyunsaturates to saturates) is evident in the 1:1, i.e., 50–50 milkfat-soybean oil combination which was used to produce one of the filled milks described in Example 6. This 1:1 combination showed excellent natural milk flavor properties in panel taste tests (see Example 9). It is also evident in Table V (see bolded numbers) that the proportions of polyunsaturated and saturated fatty acids included within the illustrated 1:2 and 2:1 ratios for soybean oil and milkfat, fall within the beneficial ranges specified in the patent claims (i.e., 15% to 40% for linoleic acid and 20% to 40% for saturated fatty acids, consistent with the findings of Sundram et al. in U.S. Pat. No. 5,578,334 and Sundram et al., U.S. Pat. No. 5,843,497).

TABLE V

FATTY ACID CONTENT OF VEGETABLE OIL AND MILKFAT BLENDS

| Weight Proportion: | Soybean Oil[a] 100% | Milkfat (Butter)[b] 100% | Soybean Oil:Milkfat Ratio | | |
|---|---|---|---|---|---|
| | | | 1:2 | 1:1 | 2:1 |
| SATs (wt %) | | | | | |
| total[c] | 14.4 | 50.5 | 38.5 | 32.5 | 26.4 |
| 4:0, 6:0, 8:0, 10:0[d] | | 7.1 | 4.7 | 3.6 | 2.4 |
| 12:0 | | 2.3 | 1.5 | 1.2 | 0.8 |
| 14:0 | 0.1 | 8.2 | 5.5 | 4.1 | 2.8 |
| 16:0 | 10.2 | 21.3 | 17.6 | 15.8 | 13.9 |
| 18:0 | 3.8 | 9.8 | 7.8 | 6.8 | 5.8 |
| MONOs (wt %) | | | | | |
| total[c] | 23.3 | 23.4 | 23.4 | 23.4 | 23.4 |
| 16:1[e] | 0.2 | 1.8 | 1.3 | 1.0 | 0.7 |
| 18:1 | 22.7 | 20.4 | 21.2 | 21.6 | 21.9 |
| 20:1 | 0.2 | | 0.1 | 0.1 | 0.1 |
| POLYs (wt %) | | | | | |
| total[c] | 63.0 | 3.0 | 23.0 | 33.0 | 43.0 |
| 18:2[f] | 54.1 | 1.8 | 19.2 | 28.0 | 36.7 |
| 18:3 | 8.5 | 1.2 | 3.6 | 4.9 | 6.1 |

[a]Reported by Archer Daniels Midland Company (Decatur, IL), product no. 86-070-0
[b]Reported in Agriculture Handbook No. 8-4, U.S. Department of Agriculture; Science and Education Administration, revised June 1979.
[c]Total fatty acid content, reported in Agriculture Handbook No. 8-4, U.S. Department of Agriculture; Science and Education Administration, revised June 1979.
[d]Saturated fatty acids having the indicated number of carbon atoms, and no C=C unsaturations
[e]Monounsaturated fatty acids having 16, 18 or 20 carbon atoms, and one C=C unsaturation
[f]Polyunsaturated fatty acids having 18 carbon atoms, and two or three C=C unsaturations

EXAMPLE 4

Modified Fluid Milk Products

Preparation of 1% Low-Fat Milks with and without Soybean Oil

Purpose of Test: To find suitable ingredients and methods for assembling a soybean oil-filled milk.

Materials and Methods: Pasteurized non-fat (skim) milk containing 2,000 IU per quart vitamin A palmitate and 400 IU per quart vitamin $D_2$ was obtained from the H.P. Hood Corporation (Charlestown, Mass). Different fat-containing pre-mix formulations were then added and blended into portions of the skim milk to make two different milks. The milks were then re-pasteurized, homogenized, cooled to 40° F., packaged in squat quart translucent high density polyethylene (HDPE) blow-molded bottles (Shelburne Plastics, Inc.), and stored in the dark at 38° F. Initially, two milks (I and II) were formulated: Milk I: Regular 1% milkfat-containing milk (all percentages are weight percentages unless otherwise specified) was formulated by adding the appropriate amount of 40% milkfat-containing cream. Milk II: A 1% filled milk containing a 50–50 combination of milkfat and soybean oil was prepared by adding 1 part of a 20% fat-containing cream to 19 parts of skim milk. The 20% cream (100 g) was prepared by blending 10 g soybean oil, 70 g whole milk containing 3.25% milkfat, 19.3 g of 40% milkfat-containing cream, 0.3 g emulsifier (mono- and diglycerides). For vitamin E-containing Milk II, tocopherol acetate (synthetic tocopherol acetate from Roche Vitamins, Inc) was added to this cream at a level that would produce 200 IU per quart of milk. The soybean oil (soybean salad oil, product no. 86-0700, Archer Daniels Midland Company, Decatur, Ill.) had been freshly refined and deodorized within approximately one week of use, had been sparged with nitrogen gas, and shipped to its destination under a blanket of nitrogen. Subsequently, after off-loading the oil, it was held in a storage tank under a blanket of nitrogen, refrigerated and stored in the dark to minimize development of any off-flavors.

Results: Initial testing of the pasteurized, homogenized filled milk (containing the 50–50 combination of milkfat and soybean oil) over a 14 day interval (standard shelf-life for milk) showed that its fat had no more tendency to separate from the skim milk than did the fat in the regular 1% milkfat-containing milk. Also, with the 50–50 formulation, there was no obvious vegetable oil flavor or oily mouthfeel (or any other off-flavor) to compromise the quality of the milk (see tast panel data below).

EXAMPLE 5

Limited Shelf-Life of 1% Low-Fat Milk Containing Soybean Oil:

Tocopherol Acetate does not Protect Milk Flavor

Purposes of Test: To determine whether the presence of soybean oil in the homogenized fat constituent of a filled milk significantly diminishes the shelf-life of milk (as measured in a 200 footcandle-illuminated refrigerated storage case), and whether the presence of vitamin E [in the form of oil-soluble tocopherol acetate (200 IU/quart) in the homogenized fat portion of the filled milk] can significantly increase the shelf-life of the milk.

Materials and Methods: Milks I and II (see Example 4 above) with and without tocopherol acetate were prepared and packaged in translucent HDPE plastic bottles, and stored cold under standard lighting conditions (38° F., 200 footcandles illumination from two General Electric Corporation model no. GE SPX35 fluorescent lamps measured by a GE model 214 light meter). After 12 hours storage, the milks were evaluated for flavor deterioration by two expert tasters who had demonstrated the ability to detect oxidized flavors in milks. The rating system for flavor was as follows: 5=very good, 4=very slightly oxidized, 3=slightly oxidized, 2=oxidized, 1=very oxidized (poor flavor). Control samples of the milks were frozen and stored (–4° F.) in the dark.

Results: With exposure of 1% milkfat-containing regular milk to visible light, the presence of tocopherol acetate in the fat portion of the milk did nothing to prevent gradual flavor degradation. In fact, the regular 1% milk (Milk I) scored 3.5 (based upon the average of the two tasters) regardless of whether tocopherol acetate was present or absent. Likewise, tocopherol acetate provided no flavor protection for the 50–50 filled milk (Milk II) which contained 0.5% milkfat and 0.5% soybean oil. In fact, after the 12 hour storage period under fluorescent lights, flavor in this milk was degraded much more severely than the regular 1% milk. Either with or without tocopherol acetate, the 50–50 milk scored only a 1 (very oxidized) based upon the two tasters. This rapid and unacceptable flavor degradation indicates that natural, i.e., non-hydrogenated, soybean oil renders the milk very susceptible to developing oxidized off-flavors. Control samples of both milks (with and without tocopherol acetate) which had been kept frozen and in the dark showed no flavor deterioration (ratings of 5).

Conclusion: Storage in the dark (or perhaps low temperature) prevented flavor deterioration in these milk products. Such storage will be especially important in the case of milks containing soybean oil because of their greater perishability. Additional experiments should distinguish between light and temperature as being significant factors affecting flavor stability.

EXAMPLE 6

Shelf-Life of 1% Low-Fat Milks with Tocopherol Acetate (Regular Milkfat Milk and 50–50 Soybean Oil-Milkfat Milk):

Importance of Avoiding Visible Light during Storage

Purpose of Test: To determine the importance of visible light (from fluorescent bulbs) and refrigeration on the shelf-life of polyunsaturated fat-filled milk during storage.

Materials and Methods: Same as in Example 5, with milks stored refrigerated under fluorescent lights, except that the control samples of milks I and II were stored refrigerated (38° F.) and in the dark, rather than frozen at –4° F.

Results: As in Example 5, the presence of tocopherol acetate did nothing to protect the flavor stability of milk II (see Example 4 for compositions). After 12 hours, milk I (with milkfat) scored a 4 for flavor while milk II (with soybean oil and milkfat) scored only a 1 (fully oxidized flavor). However, simple darkness during refrigerated storage of both milks was sufficient to provide at least a 14 day shelf-life for the milks. No off-flavors were detectable after 14 days in the dark, and the overall flavor scores of 5 were the same as when the milks were produced.

Conclusions: The addition of substantial levels of tocopherol acetate (200 IU/quart) is not helpful in preventing oxidized flavor development in milks containing either milkfat, or a blend of milkfat and soybean oil. The 50–50 blend of milkfat and soybean oil, even when refrigerated, is very susceptible to oxidized flavor development when exposed to fluorescent lights commonly encountered in supermarkets. In the absence of light, this milkfat-soybean oil blend, when refrigerated, exhibits excellent flavor stability throughout a normal 14 day shelf-life. However, less than 12 hours was required to develop off-flavors during exposure of the product to 200 footcandles fluorescent light. Accordingly, to achieve a 14 day shelf-life, it will be important to either store the milk in the dark most of the time, or alternatively, select a milk container having reduced light transmission (increased optical density) over the visible region of the light spectrum. For example, it would be prudent to reduce the transmission of light to less than 10% of the visible light transmitted through the translucent HDPE milk bottles used herein.

EXAMPLE 7

Shelf-Life of 1% Low-Fat Milks with Vitamin C (Regular Milkfat Milk and 50–50 Soybean Oil-Milkfat Milk):

Avoiding Visible Light during Storage

Purpose of Test: To determine whether vitamin C (ascorbic acid) is any more effective than tocopherol acetate in protecting soybean oil-containing milk from visible light (fluorescent lights) during refrigerated storage.

Materials and Methods: Same as in Example 6, except tocopherol acetate was replaced with ascorbic acid, 100 mg per quart. Again, milks I and II were stored refrigerated (38° F.) and exposed to 200 footcandles fluorescent lighting, while the control samples were stored refrigerated and in the dark.

Results: As in Example 6 (tocopherol acetate), the presence of ascorbic acid did nothing to protect the flavor of milks I and II. After 12 hours storage under fluorescent lights, Milk I (with only milkfat) scored a 3.5 and Milk II (with soybean oil and milkfat) scored only a 1. With the control milks, as in Example 3, simple darkness during refrigeration was sufficient to provide at least a 14 day shelf-life regardless of whether ascorbic acid was present or absent. After 14 days of dark storage, the overall flavor scores (5) were the same as when the milks were produced.

Conclusions: The addition of substantial levels of ascorbic acid (100 mg/quart) is not helpful in preventing oxidized flavor development in milks containing either milkfat, or a blend of milkfat and soybean oil. Milk II containing the 50–50 blend of milkfat and soybean oil, even when refrigerated, remains very susceptible to oxidized flavor development when exposed to fluorescent lights. Again, to obtain good shelf-life, it will be important to either store the milk in the dark, or alternatively, select a milk container having reduced light transmission (increased optical density) over the visible region of the light spectrum.

EXAMPLE 8

Effect of Packaging on the Development of Oxidized Flavor in Milk Containing a 50–50 Blend of Milkfat and Non-Hydrogenated Soybean Oil When Exposed to Fluorescent Light:

Test of Translucent, Colored Translucent, Semi-Opaque, and Opaque Jugs

Purpose of Test: To determine what type of packaging is necessary to protect a polyunsaturated fat-containing filled milk from oxidizing under fluorescent light encountered under normal refrigerated storage conditions, in which the milk contained 1% by weight of a 50–50 blend of milkfat and non-hydrogenated soybean oil. The milk also contained 200 IU per quart of tocopherol acetate.

Materials and Methods: Milk preparation conditions were the same as for milk II in Examples 4 and 5, except that samples of the 50–50 fat blend milk were stored refrigerated in a variety of different one-half gallon jugs and cartons including:

(i) a series of standard translucent HDPE milk jugs which were either wrapped in four thicknesses of different colors of cellophane (red, yellow, green, blue and clear), providing for exposure of the milk to different portions of the visible light spectrum, or alternatively, left unwrapped as a control (Table VI, see below).

(ii) semi-opaque Light-Block Bottles™ (HDPE jugs, H.P. Hood Inc., Chelsea, Mass.), and (iii) opaque paperboard half-gallon milk cartons (International Paper Company).

Light Transmission Properties of Containers: The white pigmented Light-Block Bottles™ (one-half gallon HDPE white blow-molded jugs) were tested for their degree of opacity to light. They were shown to transmit between approximately 10% and 15% of visible light between the wavelengths of 500 nm and 700 nm, and to block essentially all light below 400 nm. The paperboard cartons, on the other hand (polyethylene-coated paperboard), transmitted only between 1% and 3% of visible light in the 450–700 nm wavelength range, and blocked essentially all light below 450 nm.

Table VI provides spectral transmission measurements for four layers of various colored cellophane wrappings (and a clear cellophane "control"), used to over-wrap translucent HDPE milk jugs containing the 50–50 soybean oil-milkfat blend-containing milk. Percent light transmittance as a function of the wavelength was measured in an Hitachi model 2000 scanning spectrophotometer. Flavor stability results for the milk are presented in Table III. To monitor flavor stability in the dark, one of the translucent HDPE milk jugs was placed in a closed, fully opaque cardboard box, and stored in a dark walk-in refrigerator at 38° F. throughout the experiment. Except for this "dark" sample, all other samples were placed in an open refrigerated box maintained at 38° F. under two General Electric Corporation model no. GE SPX35 fluorescent lamps adjusted to produce a light level of approximately 200 footcandles measured with a GE model 214 light meter as in Example 2. These illuminated samples included milk placed in the paperboard carton and the Light-Block Bottle™, a HDPE jug described above, as well as a set of the cellophane-wrapped translucent HDPE milk jugs also described above. All of the half-gallon milk containers were placed on their sides to get a relatively constant light exposure among all of the bottles (210 footcandles±10%).

Samples of milk were removed from each milk jug or carton for flavor evaluation every four hours over a twenty-four hour period (see Table VII). All nine samples of milk were numbered and "blind" taste-tasted by three expert tasters who had demonstrated the ability to detect and quantify oxidized flavors in dairy products. The intensity of oxidized flavor was scored on a scale from 5 to 1, with 5 representing the absence of any detectable off-flavor, and 1 representing a very oxidized unpleasant flavor. Test results for the milk samples are ordered from best to worst. The 24 hour measurement for the red cellophane-wrapped jug (marked by *) appeared to be inconsistent with the rest of the data, and was not included in the averaging calculation.

Conclusions: Filled milk containing a substantial proportion of the fat as non-hydrogenated vegetable oil (e.g., a 50–50 blend of soybean oil and milkfat) is very vulnerable to developing off-flavors when exposed to visible light of almost any wavelength. Exposure of such milk to visible light intensities of only approximately 20–30 footcandles (10%–15% light transmission into a HDPE Light-Block Bottle™ from 200 footcandle fluorescent lighting) causes oxidized flavor development in less than 8 hours (see Table VII, sample 6). By contrast, paperboard milk cartons transmitting only approximately 2% of the incident light proved to be superior, and a very effective packaging material for preventing development of off-flavors (see Table VII, sample 2). Neither the white pigmented HDPE jug (sample 6) nor the translucent jugs wrapped in colored cellophanes which transmitted only selected portions of the visible spectrum (see Table VI), provided adequate protection for such milks. It is estimated that to provide a reasonable level of flavor protection (in illuminated and refrigerated storage units), containers for packaging milk should transmit less than 10%, and preferably less than 5% of incident visible light between the wavelengths of 350 nm and 700 nm. Fully opaque or nearly opaque milk containers such as paperboard cartons (and refrigeration) provide a practical means for protecting the flavor and mouthfeel of polyunsaturated fat-containing milk, as well as other polyunsaturated fat-containing dairy products such as soybean oil-filled ice cream, yogurt and the like.

TABLE VI

Percentage Light Transmission Through Colored Cellophane Wrappings

|  | Red | Yellow | Green | Blue | Clear |
|---|---|---|---|---|---|
| Wavelength (nm) | | | | | |
| 300 | 1.7 | 8.3 | 0.7 | 4.0 | 55 |
| 320 | 2.2 | 20 | 0.5 | 1.4 | 56 |
| 340 | 4.5 | 28 | 0.5 | 1.1 | 59 |
| 360 | 9.1 | 23 | 0.6 | 1.9 | 60 |
| 380 | 4.9 | 14 | 1.3 | 5.8 | 60 |
| 400 | 1.4 | 5.5 | 2.0 | 19 | 62 |
| 420 | 0.6 | 1.9 | 1.6 | 28 | 62 |
| 440 | 0.7 | 1.5 | 2.3 | 35 | 63 |
| 460 | 0.7 | 3.0 | 5.0 | 39 | 63 |
| 480 | 0.4 | 9.3 | 14 | 40 | 63 |
| 500 | 0.0 | 16 | 20 | 38 | 65 |
| 520 | 0.0 | 40 | 37 | 32 | 65 |
| 540 | 0.0 | 49 | 35 | 22 | 65 |
| 560 | 0.0 | 51 | 21 | 11 | 65 |
| 580 | 0.1 | 51 | 9.3 | 4.6 | 66 |
| 600 | 24 | 52 | 3.5 | 2.8 | 66 |
| 620 | 41 | 52 | 1.8 | 2.5 | 66 |
| 640 | 46 | 52 | 1.8 | 3.0 | 66 |
| 660 | 49 | 52 | 2.7 | 5.1 | 66 |
| 680 | 50 | 54 | 4.0 | 5.6 | 66 |
| 700 | 51 | 54 | 4.3 | 3.9 | 65 |

TABLE VI

Oxidized Flavor Development During Fluorescent Light Exposure

| | | | Exposure Time | | |
|---|---|---|---|---|---|
| Packaging | 4 Hr. | 8 Hr. | 12 Hr. | 24 Hr. | 24 Hr. Avg. (4, 8, 12, 24) |
| 1. HDPE (dark storage-control) | 5.0 | 4.7 | 5.0 | 5.0 | 4.9 |
| 2. Paperboard Carton | 5.0 | 4.7 | 4.7 | 4.3 | 4.7 |
| 3. Blue Wrapped | 4.7 | 5.0 | 2.7 | 3.7 | 4.0 |
| 4. Green Wrapped | 5.0 | 2.7 | 3.3 | 2.0 | 3.3 |
| 5. Red Wrapped | 3.7 | 3.0 | 2.7 | (4.7)* | 3.1 |
| 6. HDPE Light-Block Bottle ™ | 3.7 | 2.3 | 3.0 | 2.3 | 2.8 |
| 7. Yellow Wrapped | 2.0 | 2.3 | 3.0 | 2.0 | 2.3 |
| 8. Clear Wrapped (control) | 3.0 | 2.3 | 2.0 | 1.7 | 2.3 |
| 9. Unwrapped (control) | 3.3 | 2.3 | 1.7 | 1.3 | 2.2 |

EXAMPLE 9

Panel Testing for Taste and Mouthfeel of Low-Fat (1%) Milks Containing Either 100% Milkfat, 100% Soybean Oil or a 50–50 Combination Thereof:

50% Milkfat in the Presence of 50% Soybean Oil Provides Natural Milk Flavor

Purpose of Test: To determine consumer-acceptability of various 1% fat-containing milks:

I. 1% soybean oil-filled milk; II. 1% regular milkfat; III. 0.5% soybean oil plus 0.5% regular milkfat Materials and Methods: Milks were prepared as in Example 4. In addition, a filled milk containing 1% natural soybean oil (without any milkfat) was also produced. All milks contained 200 IU of tocopherol acetate. A blind tasting was conducted in which numbered samples of the different milks were served cold (38–42 F.) to 62 individual subjects whose only qualification was that they consumed a minimum of at least one serving of milk per week. The average "consumption minimum" for the 62 subjects was 4 servings of milk per week. Individuals were randomly split into two groups and asked to taste and compare two milk samples, and to rate the flavor (taste and aftertaste) and mouthfeel (sensory fullness, richness) of each milk on a scale from 1 to 10 with 1 being poor and 10 being excellent. All individuals in both groups unknowingly received regular 1% milkfat-containing milk (II) as a baseline or control. In group A, thirty-two individuals received and compared milk I (100% soybean oil) versus milk II (regular), while in group B, thirty-two individuals received and compared milk III (soybean oil-milkfat combination) versus milk II (regular).

Group A Results: Based upon averaging the 32 test scores for subjects in group A, the regular 1% milkfat milk received a score of 7.6 for flavor and 7.3 for mouthfeel while the 1% soybean oil milk received a score of only 5.4 for flavor and 6.2 for mouthfeel. The significantly diminished flavor score (5.4 versus 7.6) indicates that elimination of milkfat leaves a "flavor void" in the milk. Typical comments which described the shortcomimgs of the 1% soybean oil (versus the 1% milkfat-containing milk) were as follows:

1. "a bit plain" (versus "creamier, more tasty")
2. "lighter" (versus "creamy, sweeter")
3. "no flavor, thin like skim milk" (versus "plain, very good, fresh")
4. "a little watery tasting (versus "tastes normal, good")
5. "sort of skim, thin" (versus "milky, fuller, creamier")

6. "aftertaste reminds me of baby formula" (versus "nice and rich-tasting")
7. "very thin, gross aftertaste" (versus "much better, tastes almost like whole milk")

Group A Conclusion: On the positive side, the 1% freshly refined soybean oil ingredient emerged from this group A test as a transparent-tasting ingredient, i.e., one which did not alter flavor or contribute any off-flavor to the milk. At the same time, when used alone, it failed to produce the regular milk flavor tasted in the 1% milkfat-containing milk. Applicants believe that the subjects' descriptions of "natural" and "creamy and rich" attributed to the flavor of regular 1% milkfat-containing milk reflect the flavor of the diverse fatty acids present in milkfat triglycerides, particularly the shorter chain fatty acids which are 4 to 10 carbons in length. Some of these fatty acids are certainly released in the mouth by the action of lingual lipase. These short chain fatty acids which would contribute to the distinctive aftertaste of milk, are entirely lacking in soybean oil and other vegetable oils whose fatty acids are predominantly sixteen and eighteen carbons in length.

Group B Results: Averaging the 32 subjects and their scoring in group B, regular 1% milkfat milk (milk II) received a score of 7.6 for flavor and 7.3 for mouthfeel (identical to the scoring from Group A subjects for the same regular 1% milkfat milk), while the blended fat-containing milk (milk III having 0.5% soybean oil plus 0.5%milkfat) received a score of 6.7 for flavor and 6.8 for mouthfeel. The excellent scores for milk III are respectively 88% and 93% as high as the scores for regular milk II. Typical comments which described milk III versus milk II were as follows:
1. "thick and milky" (versus "bit thin")
2. "bit thin but still tasty" (versus "milky and creamy,")
3. "a lot of feel, but not too much taste" (versus "has lots of aftertaste")
4. "both very good, almost can't tell the difference"
5. "slightly different but good" (versus "traditional taste")
6. "could not tell the difference between the two"
7. "less flavor than whole milk, light mouthfeel" (versus "more like whole milk")
8. "very good, less rich than the other" (versus very rich flavor)
9. "nice aftertaste in back of mouth, thin and clean (versus less aftertaste but good, mouthfeel same)

Group B Conclusion: Unlike the 100% soybean oil-containing milk, milk III which contains the 50–50 blend of milkfat and soybean oil, has a taste and mouthfeel which is remarkably similar to milk II, the regular milk. In fact, considering some of the comments of the subjects, there is significant taste and mouthfeel ambiguity between milks II and III (cf. reports of subjects #1 and #2 which are nearly the opposite of one another). Many individuals rate the milks as approximately equal. Some individuals find that the blended fat composition produces a thinner mouthfeel milk, while others find the opposite. The presence of 0.5% milkfat, when added to 0.5% soybean oil, appears to restore much of the taste and aftertaste of regular 1% milkfat milk. This flavor is lost when all of the milkfat is replaced with soybean oil. Applicants suggest above that "milkfat flavor" may be partially derived from lingual lipase cleavage of flavorful short to medium chain fatty acids from milkfat triglyceride molecules in the mouth. It is generally accepted that sensory intensity for many flavors varies with the logarithm of the concentration of that flavor. If so, a 50% reduction in milkfat concentration (from 1% to 0.5%) would diminish the level of milkfat flavor to perhaps 70% of its original intensity level. Importantly, the test scores suggest that the 0.5% milkfat content in a 1% fat-containing milk, is sufficient for achieving widespread consumer satisfaction.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One of ordinary skill in the art would readily appreciate that the present invention is well adapted to carry out the objects and obtain the ends and advantages mentioned, as well as those inherent therein. The specific methods and compositions described herein as presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention. For example, those skilled in the art will recognize that the invention may suitably be practiced using various sources of vegetable oils in the described blends.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is not intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group. For example, if there are alternatives A, B, and C, all of the following possibilities are included: A separately, B separately, C separately, A and B, A and C, B and C, and A and B and C. Thus, the embodiments expressly include any subset or subgroup of those alternatives, for example, any subset of the types of fatty acids or vegetable oils. While each such subset or subgroup could be listed separately, for the sake of brevity, such a listing is replaced by the present description.

Further, in particular embodiments, the various selections of components described above, may be independently combined where the selections are compatible. Those skilled in the art will readily recognize such compatibility. Thus, for example, the dairy product, milkfat, vegetable oil, composition of fat portion or substitute fat, emulsifier, and/or packaging may be independently selected and combined, recognizing that not all of those items need be specified in a claimed embodiment.

While certain embodiments and examples have been used to describe the present invention, many variations are possible and are within the spirit and scope of the invention. Such variations will be apparent to those skilled in the art upon inspection of the description and claims herein.

Other embodiments are within the following claims.

What is claimed is:

1. A method of aiding a person to increase the HDL concentration and the HDL/LDL concentration ratio in the serum of said person by providing a cholesterol-free dietary fat composition comprising a blend of at least one saturated fat and at least one polyunsaturated fat, wherein the ratio of polyunsaturated fatty acids to saturated fatty acids in said fat composition is from 0.5:1 to 2:1, and said dietary fat composition comprises between 20% and 40% by weight saturated fatty acids comprising lauric acid or palmitic acid or both, between 15% and 40% by weight linoleic acid, and no more than 1% by weight elaidic acid or other unnatural trans fatty acid;

wherein said HDL concentration and said HDL/LDL concentration ratio will increase when the daily dietary fat accounts for between 15% and 50% of the total dietary energy and contains between 20% and 40% by weight saturated fatty adds comprising lauric acid or palmitic add or both and between 15% and 40% by weight linoleic acid.

2. The method of claim 1, wherein said ratio of polyunsaturated fatty acids to saturated fatty acids is 1:1±20%.

3. The method of claim 1, wherein said fat composition further comprises between 20% and 50% by weight oleic acid.

4. The method of claim 1, comprising approximately 30% by weight palmitic acid and approximately 30% by weight linoleic acid plus linolenic acid.

5. The method of claim 1, wherein said polyunsaturated fat comprises at least one polyunsaturated vegetable oil selected from the group consisting of corn oil, sunflower oil, safflower oil, soybean oil, cottonseed oil, canola oil, and peanut oil; and said saturated fat comprises at least one saturated vegetable oil selected from the group consisting of palm fat, coconut fat and cocoa butter.

6. The method of claim 5, wherein said palm fat is selected from the group consisting of palm oil, palm olein, and palm kernel oil.

7. The method of claim 1, wherein said polyunsaturated fat consists essentially of soybean oil, and said saturated fat consists essentially of palm fat.

8. The method of claim 1, wherein said fat composition further comprises at least one polyunsaturated fatty acid selected from the group consisting of alpha-linolenic acid, eicosapentenoic acid (EPA), and docosahexenoic acid (DHA).

9. The method of claim 1, wherein said blend consists of a mixture of two vegetable fats.

10. The method of claim 1, wherein said fat composition comprises less than 5% by weight stearic acid.

11. The method of claim 1, wherein said saturated fatty acids are predominantly palmitic acid.

12. The method of claim 1, wherein greater than 50% by weight of said saturated fatty acids is palmitic acid.

13. The method of claim 1, wherein the weight ratio of said polyunsaturated fats to saturated fats is in the range 0.5:1 to 2:1.

14. The method of claim 13, wherein said weight ratio of polyunsaturated fats to saturated fats is approximately 1:1.

15. The method of claim 13, wherein said weight ratio of polyunsaturated fats to saturated fats is approximately 1.5:1.

16. The method of claim 13, wherein said weight ratio of polyunsaturated fats to saturated fats is approximately 1:1.5.

17. The method of claim 1, wherein said dietary fat composition includes at least one saturated fat selected from the group consisting of palm oil, palm olein, palm kernel oil, coconut fat and coca butter; and at least one unsaturated fat selected from the group consisting of corn oil, sunflower oil, safflower oil, cottonseed oil, canola oil, and peanut oil.

18. The method of claim 1, wherein said dietary fat composition includes at least one saturated fat selected from the group consisting of palm olein, palm kernel oil, coconut fat and coca butter; and at least one unsaturated fat selected from the group consisting of corn oil, sunflower oil, safflower oil, soybean oil, cottonseed oil, canola oil, and peanut oil.

19. The method of claim 1, wherein the weight ratio of polyunsaturated fats to saturated fats of said dietary fat composition is not 1:1.

20. A method of aiding a person to increase the HDL concentration and the HDL/LDL concentration ratio in the serum of said person by providing a cholesterol-free prepared food product that is prepared using a blend of saturated fat and polyunsaturated fat forming a dietary fat composition, wherein the ratio of polyunsaturated fatty acids to saturated fatty acids in said dietary fat composition is from 0.5:1 to 2:1, and said dietary fat composition comprises between 20% and 40% by weight saturated fatty acids comprising lauric acid or palmitic acid or both, between 15% and 40% by weight linoleic acid, and no more than 1% by weight elaidic acid or other unnatural trans fatty acid;

wherein said HDL concentration and said HDL/LDL concentration ratio will increase when the daily dietary fat accounts for between 15% and 50% of the total dietary energy and contains between 20% and 40% by weight saturated fatty acids comprising lauric acid or palmitic acid or both and between 15% and 40% by weight linoleic acid.

21. The method of claim 20, wherein said prepared food product is a blended food product.

22. The method of claim 21, wherein said blended food product is selected from the group consisting of salad dressing, margarine, and mayonnaise.

23. The method of claim 20, wherein said prepared food product is a baked prepared food.

24. The method of claim 20, wherein said prepared food product is a dairy product.

25. The method of claim 20, wherein said ratio of polyunsaturated fatty acids to saturated fatty acids is 1:1±20%.

26. The method of claim 20, wherein said dietary fat composition further comprises between 20% and 50% by weight oleic acid.

27. The method of claim 20, comprising approximately 30% by weight palmitic acid and approximately 30% by weight linoleic acid plus linoleic acid.

28. The method of claim 20, wherein said polyunsaturated fat comprises at least one polyunsaturated vegetable oil selected from the group consisting of corn oil, sunflower oil, safflower oil, soybean oil, cottonseed oil, canola oil, and peanut oil; and said saturated fat comprises at least one saturated vegetable oil selected from the group consisting of palm fat, coconut fat and cocoa butter.

29. The method of claim 28, wherein said palm fat is selected from the group consisting of palm oil, palm olein, and palm kernel oil.

30. The method of claim 20, wherein said polyunsaturated fat consists essentially of soybean oil, and said saturated fat consists essentially of palm fat.

31. The method of claim 20, wherein said dietary fat composition further comprises at least one polyunsaturated fatty acid selected from the group consisting of alpha-linolenic acid, eicosapentenoic acid (EPA), and docosahexenoic acid (DHA).

32. The method of claim 20, wherein said blend consists of a mixture of two vegetable fats.

33. The method of claim 20, wherein said dietary fat composition comprises less than 5% by weight stearic acid.

34. The method of claim 20, wherein said saturated fatty acids are predominantly palmitic acid.

35. The method of claim 20, wherein greater than 50% by weight of said saturated fatty acids is palmitic acid.

36. The method of claim 20, wherein the weight ratio of said polyunsaturated fats to saturated fats is in the range 0.5:1 to 2:1.

37. The method of claim 36, wherein said weight ratio of polyunsaturated fats to saturated fats is approximately 1:1.

38. The method of claim 36, wherein said weight ratio of polyunsaturated fats to saturated fats is approximately 1.5:1.

39. The method of claim 36, wherein said weight ratio of polyunsaturated fats to saturated fats is approximately 1:1.5.

40. The method of claim 20, wherein said prepared food product includes at least one saturated fat selected from the group consisting of palm oil, palm olein, palm kernel oil, coconut fat and coca butter; and at least one unsaturated fat selected from the group consisting of corn oil, sunflower oil, safflower oil, cottonseed oil, canola oil, and peanut oil.

41. The method of claim 20, wherein said prepared food product includes at least one saturated fat selected from the group consisting of palm olein, palm kernel oil, coconut fat and coca butter; and at least one unsaturated fat selected from the group consisting of corn oil, sunflower oil, safflower oil, soybean oil, cottonseed oil, canola oil, and peanut oil.

42. The method of claim 20, wherein the weight ratio of polyunsaturated fats to saturated fats of said prepared food product is not 1:1.

* * * * *